United States Patent
Kuramoto

(10) Patent No.: US 9,582,878 B2
(45) Date of Patent: Feb. 28, 2017

(54) IMAGE PROCESSING DEVICE AND OPERATION METHOD THEREFOR

(71) Applicant: FUJIFILM Corporation, Tokyo (JP)

(72) Inventor: Masayuki Kuramoto, Ashigarakami-gun (JP)

(73) Assignee: FUJIFILM Corporation, Tokyo (JP)

( * ) Notice: Subject to any disclaimer, the term of this patent is extended or adjusted under 35 U.S.C. 154(b) by 0 days.

(21) Appl. No.: 15/139,940

(22) Filed: Apr. 27, 2016

(65) Prior Publication Data

US 2016/0239965 A1    Aug. 18, 2016

Related U.S. Application Data

(63) Continuation of application No. PCT/JP2014/078046, filed on Oct. 22, 2014.

(30) Foreign Application Priority Data

Oct. 28, 2013    (JP) .................. 2013-222964

(51) Int. Cl.
*G06K 9/00*    (2006.01)
*G06T 7/00*    (2006.01)
(Continued)

(52) U.S. Cl.
CPC ........ *G06T 7/0012* (2013.01); *A61B 1/00009* (2013.01); *A61B 1/00045* (2013.01);
(Continued)

(58) Field of Classification Search
None
See application file for complete search history.

(56) References Cited

U.S. PATENT DOCUMENTS 6,422,994 B1 *   7/2002   Kaneko ............. A61B 1/00009
                                                       600/160
7,328,059 B2 *   2/2008   Sevick-Muraca .... A61B 5/0059
                                                       600/431

(Continued)

FOREIGN PATENT DOCUMENTS

JP    2000-148987 A      5/2000
JP       3228627 B2     11/2001
(Continued)

OTHER PUBLICATIONS

International Search Report for PCT/JP2014/078046 mailed on Jan. 13, 2015.
(Continued)

*Primary Examiner* — Hadi Akhavannik
(74) *Attorney, Agent, or Firm* — Birch, Stewart, Kolasch & Birch, LLP

(57) ABSTRACT

A base image is created from RGB image signals. A B/G ratio between the B image signal and the G image signal is calculated, and a G/R ratio between the G image signal and the R image signal is calculated. A frequency component-enhanced image in which a frequency component corresponding to an abnormal part different from a normal part is enhanced is generated based on the base image. A composition ratio which indicates the ratio for composing the frequency component-enhanced image with the base image is set based on the B/G ratio and the G/R ratio. The frequency component-enhanced image is composed with the base image at the set composition ratio to generate a structure-enhanced image in which the structure of the abnormal part is enhanced.

17 Claims, 15 Drawing Sheets

(51) Int. Cl.
  *G02B 23/24* (2006.01)
  *H04N 7/18* (2006.01)
  *A61B 1/00* (2006.01)
  *G06T 5/00* (2006.01)
  *A61B 1/005* (2006.01)
  *A61B 1/05* (2006.01)
  *A61B 1/06* (2006.01)
  *A61B 1/273* (2006.01)
  *A61B 5/00* (2006.01)
  *G06T 7/40* (2006.01)
(52) U.S. Cl.
  CPC .............. *A61B 1/0052* (2013.01); *A61B 1/05* (2013.01); *A61B 1/0676* (2013.01); *A61B 1/273* (2013.01); *A61B 5/004* (2013.01); *A61B 5/0059* (2013.01); *A61B 5/4238* (2013.01); *G02B 23/24* (2013.01); *G06T 5/003* (2013.01); *G06T 7/408* (2013.01); *H04N 7/18* (2013.01); *G06T 2207/10024* (2013.01); *G06T 2207/10068* (2013.01); *G06T 2207/30092* (2013.01); *G06T 2207/30096* (2013.01); *G06T 2207/30101* (2013.01)

(56) References Cited

U.S. PATENT DOCUMENTS

2004/0263643 A1* 12/2004 Imaizumi ........... A61B 1/00009
                                                            348/222.1
2012/0078044 A1     3/2012 Yamaguchi et al.
2012/0253122 A1* 10/2012 Minetoma .......... A61B 1/00057
                                                            600/109

FOREIGN PATENT DOCUMENTS

JP      2003-93336 A     4/2003
JP      2012-71012 A     4/2012

OTHER PUBLICATIONS

Written Opinion of the International Searching Authority for PCT/JP2014/078046 mailed on Jan. 13, 2015.
English Translation of the International Preliminary Report on Patentability for PCT/JP2014/078046 (including PCT/IB/373 and PCT/ISA/237), issued on May 3, 2016.

* cited by examiner

FIG. 12

|  | g1(B/G RATIO, G/R RATIO) | g2(B/G RATIO, G/R RATIO) | g3(B/G RATIO, G/R RATIO) | g4(B/G RATIO, G/R RATIO) |
|---|---|---|---|---|
| B/G RATIO, G/R RATIO — SECOND RANGE | 100% | 0% | 0% | 0% |
| THIRD RANGE | 0% | 100% | 0% | 0% |
| FOURTH RANGE | 0% | 0% | 100% | 0% |
| FIFTH RANGE | 0% | 0% | 0% | 100% |
| NEITHER OF SECOND TO FIFTH RANGES | 0% | 0% | 0% | 0% |

IMAGE PROCESSING DEVICE AND OPERATION METHOD THEREFOR

CROSS-REFERENCE TO RELATED APPLICATIONS

This application is a Continuation of PCT International Application No. PCT/JP2014/078046 filed on Oct. 22, 2014, which claims priority under 35 U.S.C §119(a) to Japanese Patent Application No. 2013-222964 filed Oct. 28, 2013. The above application is hereby expressly incorporated by reference, in its entirety, into the present application.

BACKGROUND OF THE INVENTION

1. Field of the Invention

The present invention relates to an image processing device which processes an image for use at the time of diagnosis of atrophic gastritis, and an operation method therefor.

2. Description Related to the Prior Art

In a medical field, diagnosis or the like using an endoscope system comprising a light source device, an electronic endoscope, and a processor device has been widely performed. In a recent endoscope system, with high resolution using a high-vision system, such as high sensitivity or an increase in the number of pixels of an imaging element incorporated in an electronic endoscope, a high-definition image exceeding conventional image quality has been able to be displayed. With this, it is possible to depict even a small lesion of a fine blood vessel or a mucosa very realistically.

With the realization of high-vision, since the shape or size of a lesion part is made clear, it is possible to facilitate the detection of the lesion part. However, a doctor finds the lesion part from a slight difference in color of a mucosa as well as the shape or size of the lesion part. For example, a portion which is reddish and has a slight difference in color from the mucosa is detected as an early lesion part. There is a case where the slightly reddish portion cannot be found even if high-vision is realized if just resolution is increased.

Accordingly, in Japanese Patent No. 3228627, color enhancement processing for reddening a reddish portion and whitening a white portion is performed to make a boundary of a lesion part noticeable. As in United States Patent Application Publication No. 2012/0078044 (corresponding to JP2012-71012A), the size of a discolored area different in color from a mucosa, such as a brownish area (BA), is detected, and frequency band-enhancement processing is performed according to the size of the discolored area to enhance the structure of the discolored area. The color enhancement processing or frequency band enhancement processing is performed, whereby it is possible to find a lesion part which cannot be found with just the realization of high-vision.

In recent years, a lesion part of the stomach, such as a gastric cancer, has been detected from the state of atrophic gastritis. This uses the following relationship between atrophic gastritis and the lesion part of the stomach. In a case of a normal gastric mucosal structure shown in FIG. 18A, since a mucosal layer of a surface is increased in thickness, most of light is absorbed or reflected in the mucosal layer. For this reason, as shown in FIG. 18B, it In contrast, as shown in FIG. 19A, in a case of a gastric mucosal structure in which atrophic gastritis has progressed, a mucosal layer is decreased in thickness with a decrease in the number of gastric gland cells. The change of the internal structure of the gastric mucosa with the progress of atrophic gastritis appears as changes (A) and (B) described below on an endoscopic image.

(A) A lamina muscularis mucosae of a color close to white becomes see-through, and the color of atrophic mucosa becomes a faded color compared to a normal part.

(B) In an area where there is an atrophic mucosa, when a mucosal layer is decreased in thickness with atrophy, a blood vessel of a submucosa becomes see-through (see FIG. 19B).

Accordingly, in diagnosis of a gastric lesion part based on atrophic gastritis, the degree of progress of atrophy or the boundary between a normal part and a gastritis part is determined using the two features (A) and (B) described above.

In a case where atrophy has progressed to a high degree (for example, in a case of atrophy included in a group C or a group D in an ABC examination), it is possible to observe the two features (A) and (B) described above on an endoscopic image clearly. However, in a case where atrophy has not progressed much, that is, atrophy is progressing (for example, in a case of atrophy included in a group B or a group C in an ABC examination), the difference between an atrophic part and a normal part on an endoscopic image is slight, and it is difficult to determine the degree of progress of atrophy or the boundary between a normal part and a gastritis part in some cases. Accordingly, there is a demand for making the two features (A) and (B) described above on an endoscopic image clear to make the boundary between a normal part and a gastritis part clear.

In regard to this, the application of the methods of Japanese Patent No. 3228627 and United States Patent Application Publication No. 2012/0078044 is considered. The method of Japanese Patent No. 3228627 enhances a color such that a reddish portion becomes redder, instead of enhancing change in color faded with atrophy of the stomach or change in color such that a blood vessel of a submucosa becomes see-through with atrophy of the stomach. The method of United States Patent Application Publication No. 2012/0078044 performs enhancement processing of a frequency band according to the size of the discolored area, instead of performing enhancement processing according to change in color with atrophy of the stomach.

SUMMARY OF THE INVENTION

An object of the invention is to provide an image processing device and an operation method therefor capable of performing color difference enhancement or structure enhancement according to change in color of a mucosa or the like, which may occur at the time of atrophy of the stomach due to atrophic gastritis.

An image processing device of the invention comprises an image signal input unit, a base image creation unit, a signal ratio calculation unit, a frequency enhancement unit, a composition ratio setting unit, and a composition unit. The image signal input unit inputs image signals of three colors. The base image creation unit creates a base image based on the image signals of three colors. The signal ratio calculation unit calculates a first signal ratio between the image signals of two colors among the image signals of the three colors and a second signal ratio between the image signals of two colors different from the colors for the first signal ratio. The frequency enhancement unit generates a frequency component-enhanced image, in which a frequency component corresponding to an abnormal part different from a normal part is enhanced, based on the base image. The composition ratio setting unit sets a composition ratio indicating the ratio for composing the frequency component-enhanced image with the base image based on the first signal ratio and the second signal ratio. The composition unit composes the frequency component-enhanced image with the base image at the composition ratio set by the composition ratio setting unit to generate a structure-enhanced image, in which the structure of the abnormal part is enhanced.

It is preferable that the composition ratio setting unit sets the composition ratio to "0%" for pixels where the first and second signal ratios calculated by the signal ratio calculation unit are included in a first range having a lot of the first and second signal ratios of the normal part, and sets the composition ratio to "100%" for pixels where the first and second signal ratios calculated by the signal ratio calculation unit are included in a specific range having a lot of the first and second signal ratios of the abnormal part.

It is preferable that the abnormal part is a faded mucosa, the specific range is a second range which includes a lot of the first and second signal ratios of the faded mucosa, and the first range and the second range have the same hue, and the second range has saturation lower than that in the first range. It is preferable that the abnormal part is a blood vessel area which has a blood vessel, which becomes see-through with the progress of a lesion under a faded mucosa, the specific range is a third range which includes a lot of the first and second signal ratios of the blood vessel area, and the first range and the third range have the same saturation and have different hues. It is preferable that the abnormal part is a brownish area, and the specific range is a fourth range which includes a lot of the first and second signal ratios of the brownish area. It is preferable that the abnormal part is reddened area, and the specific range is a fifth range which includes a lot of the first and second signal ratios of the reddened area. It is preferable that the image signals of the three colors are RGB image signals, and the first signal ratio is a B/G ratio between the B image signal and the G image signal, and the second signal ratio is a G/R ratio between the G image signal and the R image signal.

An image processing device of the invention comprises an image signal input unit, a color information acquisition unit, a color difference enhancement unit, a frequency enhancement unit, a composition ratio setting unit, and a composition unit. The image signal input unit inputs a color image signal. The color information acquisition unit acquires a plurality of kinds of color information from the color image signal. The color difference enhancement unit performs expansion processing for expanding the difference between a first range and a specific range different from the first range in a feature space formed by the plurality of kinds of color information to generate a color difference-enhanced image, in which the color difference between a normal part and an abnormal part is enhanced. The frequency enhancement unit generates a frequency component-enhanced image, in which a frequency component corresponding to the abnormal part is enhanced, based on the color difference-enhanced image. The composition ratio setting unit sets a composition ratio indicating the ratio for composing the frequency component-enhanced image with the color difference-enhanced image based on the plurality of kinds of color information. The composition unit composes the frequency component-enhanced image with the color difference-enhanced image at the composition ratio set by the composition ratio setting unit to generate a color difference and structure-enhanced image, in which the color difference is enhanced and the structure of the abnormal part is enhanced. It is preferable that the color image signal is image signals of three colors, and the color information acquisition unit is a signal ratio calculation unit which calculates, as the plurality of kinds of color information, the first signal ratio between the image signals of two colors among the image signals of the three colors and the second signal ratio between the image signals of two colors different from the colors for the first signal ratio.

An operation method for an image processing device of the invention comprises an input step, a base image creation step, a signal ratio calculation step, a frequency component-enhanced image generation step, a composition ratio setting step, and a composition step. In the input step, an image signal input unit inputs image signals of three colors. In the base image creation step, a base image creation unit creates a base image based on the image signals of three colors. In the signal ratio calculation step, a signal ratio calculation unit calculates a first signal ratio between the image signals of two colors among the image signals of the three colors and a second signal ratio between the image signals of two colors different from the colors for the first signal ratio. In the frequency component-enhanced image generation step, a frequency enhancement unit generates a frequency component-enhanced image, in which a frequency component corresponding to an abnormal part different from a normal part is enhanced, based on the base image. In the composition ratio setting step, a composition ratio setting unit sets a composition ratio indicating the ratio for composing the frequency component-enhanced image with the base image based on the first signal ratio and the second signal ratio. In the composition step, a composition unit composes the frequency component-enhanced image with the base image at the composition ratio set by the composition ratio setting unit to generate a structure-enhanced image, in which the structure of the abnormal part is enhanced.

An operation method for an image processing device of the invention comprises an input step, a color information acquisition step, a color difference-enhanced image generation step, a frequency component-enhanced image generation step, a composition ratio setting step, and a composition step. In the input step, an image signal input unit inputs a color image signal. In the color information acquisition step, a color information acquisition unit acquires a plurality of kinds of color information from the color image signal. In the color difference-enhanced image generation step, a color difference enhancement unit performs expansion processing for expanding the difference between a first range and a specific range different from the first range in a feature space formed by the plurality of kinds of color information to generate a color difference-enhanced image, in which the color difference between a normal part and an abnormal part is enhanced. In the frequency component-enhanced image generation step, a frequency enhancement unit generates a frequency component-enhanced image, in which a frequency component corresponding to the abnormal part is enhanced, based on the color difference-enhanced image. In the composition ratio setting step, a composition ratio setting unit sets a composition ratio indicating the ratio for composing the frequency component-enhanced image with the color difference-enhanced image based on the plurality of kinds of color information. In the composition step, a composition unit composes the frequency component-enhanced image with the color difference-enhanced image at the composition ratio set by the composition ratio setting unit to generate a color difference and structure-enhanced image, in which the color difference is enhanced and the structure of the abnormal part is enhanced.

According to the invention, it is possible to perform color difference enhancement or structure enhancement according to change in color of a mucosa or the like, which may occur at the time of atrophy of the stomach due to atrophic gastritis.

BRIEF DESCRIPTION OF DRAWINGS

For more complete understanding of the present invention, and the advantage thereof, reference is now made to the subsequent descriptions taken in conjunction with the accompanying drawings, in which:

FIG. 12 is a table showing the relationship between a B/G ratio, a G/R ratio and composition ratios g1 to g4 (B/G ratio, G/R ratio);

DESCRIPTION OF THE PREFERRED EMBODIMENTS

First Embodiment

Figure 1:
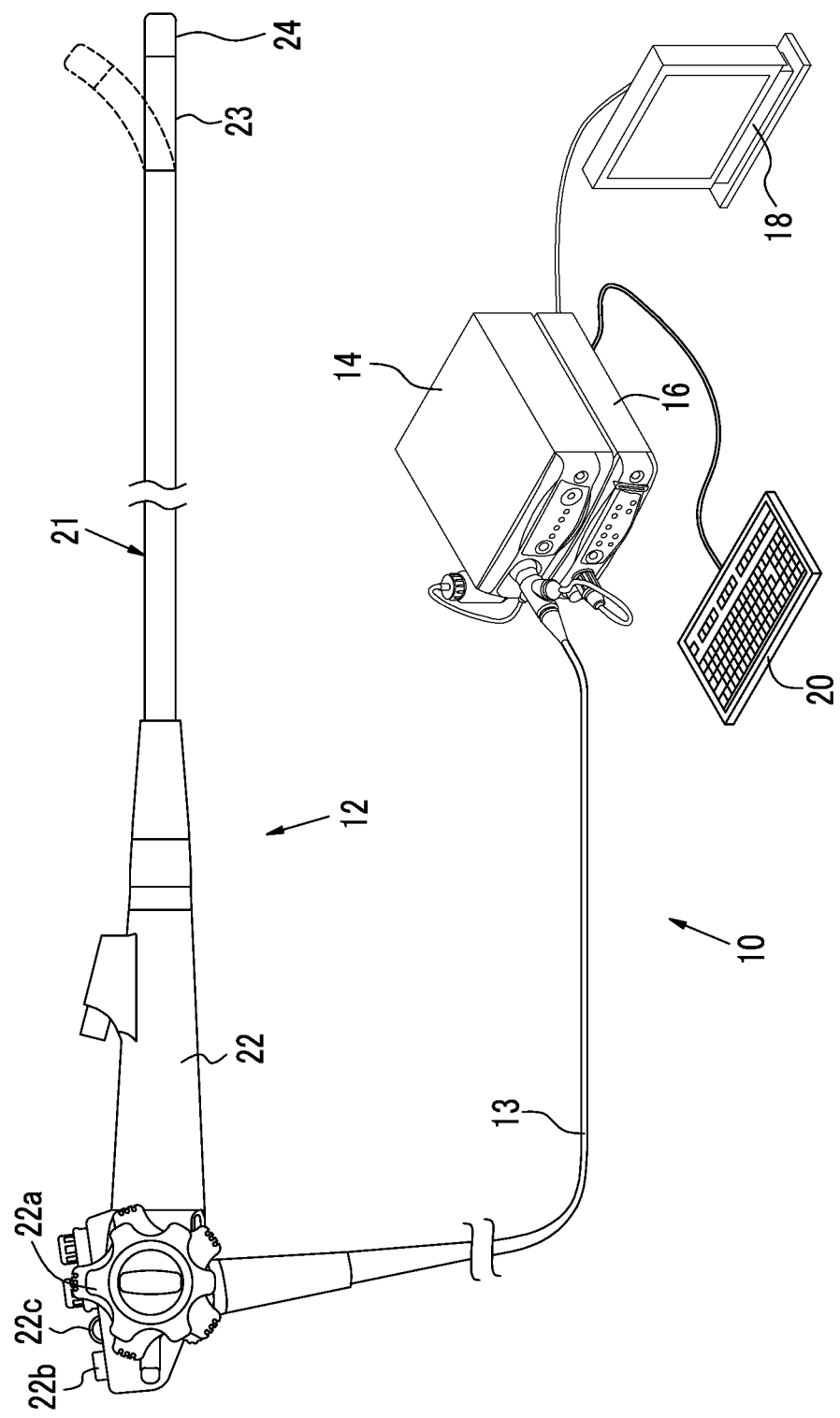
FIG. 1 is an appearance diagram of an endoscope system.

As shown in FIG. 1, an endoscope system 10 of a first embodiment has an endoscope 12, a light source device 14, a processor device 16, a monitor 18, and a console 20. The endoscope 12 is optically connected to the light source device 14 and electrically connected to the processor device 16 through a universal cord 13. The endoscope 12 has an insertion portion 21 which is inserted into a specimen, an operation portion 22 which is provided in a base portion of the insertion portion, and a bending portion 23 and a tip portion 24 which are provided on the tip side of the insertion portion 21. The bending portion 23 is bent by operating an angle knob 22a of the operation portion 22. The tip portion 24 is directed in a desired direction with a bending operation.

The operation portion 22 is provided with a mode selection SW 22b and a zoom operation portion 22c, in addition to the angle knob 22a. The mode selection SW 22b is used for a switching operation between two modes of a normal observation mode and a special observation mode. The normal observation mode is a mode in which white light is used for illumination in the specimen. The special observation mode is a mode in which bluish special light is used for illumination in the specimen, and a mode in which change in color of a mucosa, which may occur at the time of atrophy of the stomach due to atrophic gastritis, or seeing-through of a blood vessel is enhanced. The zoom operation portion 22c is used for a zoom operation to drive a zooming lens 47 (see FIG. 2) in the endoscope 12 to enlarge the specimen. In the special observation mode, white light may be used, instead of special light.

The processor device 16 is electrically connected to the monitor 18 and the console 20. The monitor 18 outputs and displays image information or the like. The console 20 functions as a user interface (UI) which receives an input operation, such as function setting. An external recording unit (not shown) which records image information or the like may be connected to the processor device 16.

Figure 2:
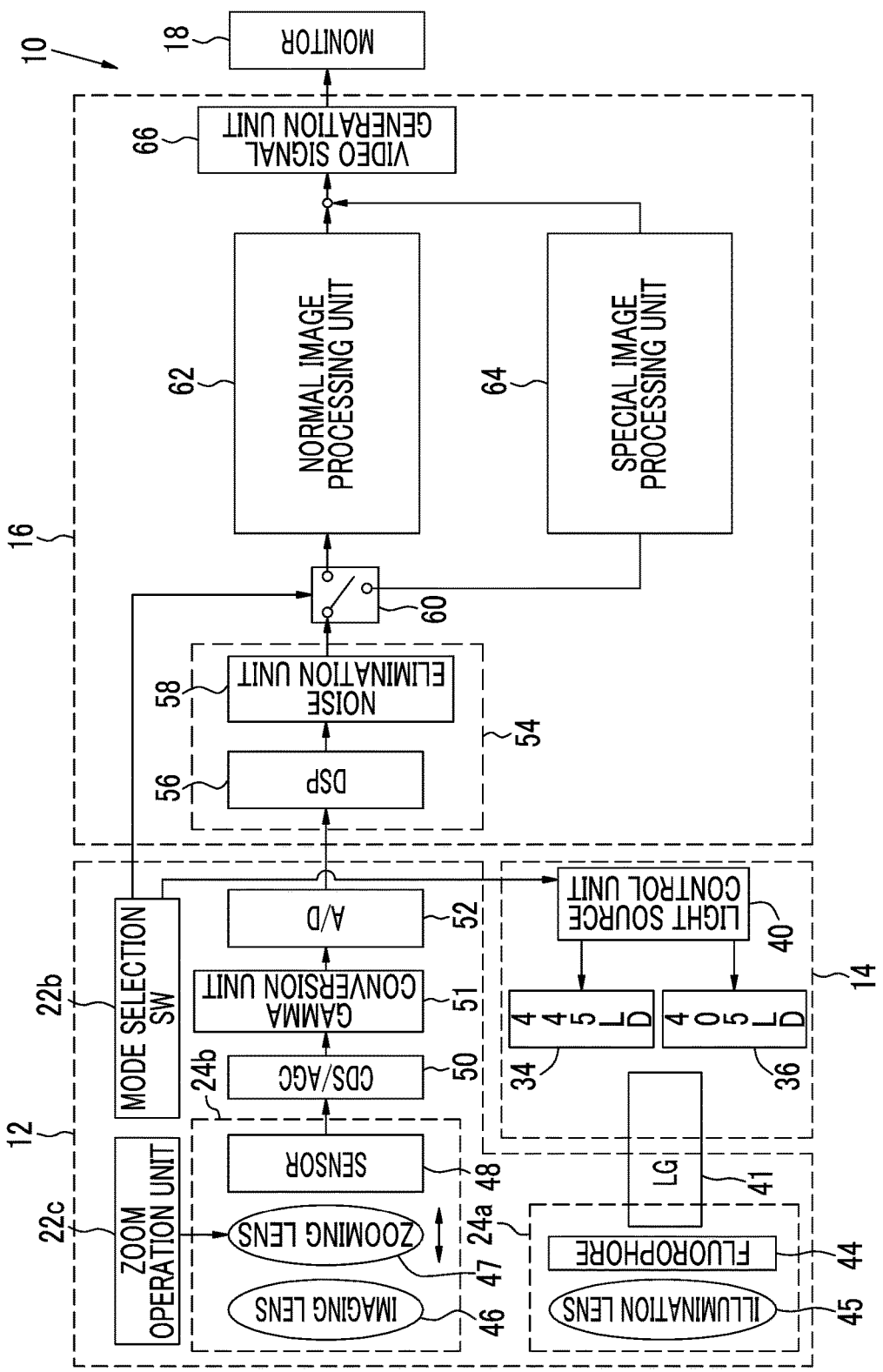
FIG. 2 is a block diagram showing the internal configuration of an endoscope system of a first embodiment.

As shown in FIG. 2, the light source device 14 comprises, as a light emitting source, a blue laser source (445 LD) 34 which emits a blue laser beam having a center wavelength of 445 nm, and a violaceous laser source (405 LD) 36 which emits a violaceous laser beam having a center wavelength of 405 nm. Light emission from the semiconductor light emitting elements of the light sources 34 and 36 is controlled individually by a light source control unit 40, and a light amount ratio of emitted light of the blue laser source 34 and emitted light of the violaceous laser source 36 is freely changed. In a case of the normal observation mode, the light source control unit 40 primarily drives the blue laser source 34, and performs control such that a small amount of violaceous laser beam is emitted. In a case of the normal observation mode, the violaceous laser source 36 may be driven. However, in this case, it is preferable to reduce the light emission intensity of the violaceous laser source 36 to a low level.

In contrast, in a case of the special observation mode, both of the blue laser source 34 and the violaceous laser source 36 are driven, and control is performed such that the light emission proportion of a blue laser beam is greater than the light emission proportion of a violaceous laser beam. It is preferable that a half width of a blue laser beam or a violaceous laser beam is about ±10 nm. For the blue laser source 34 and the violaceous laser source 36, abroad-area type InGaN-based laser diode is available, and in addition, an InGaNAs-based laser diode or a GaNAs-based laser diode is available. As the light sources described above, an illuminant, such as a light emitting diode, may be used.

The laser beam emitted from each of the light sources 34 and 36 enters a light guide (LG) 41 through optical members (none of them is shown) including a condenser lens, an optical fiber, a multiplexer, and the like. The light guide 41 is incorporated in the endoscope 12 and the universal cord 13. The blue laser beam having the center waveform of 445 nm or the violaceous laser beam having the center wavelength of 405 nm is transmitted to the tip portion 24 of the endoscope 12 through the light guide 41. As the light guide 41, a multi-mode fiber is available. As an example, a slender fiber cable which has a core diameter of 105 μm, a clad diameter of 125 μm, and a diameter φ of 0.3 to 0.5 mm including a protective layer as a sheath is available.

The tip portion 24 of the endoscope 12 has an illumination optical system 24a and an imaging optical system 24b. The illumination optical system 24a is provided with a phosphor 44 on which the blue laser beam having the center wavelength of 445 nm or the violaceous laser beam having the center wavelength of 405 nm from the light guide 41 is incident, and an illumination lens 45. With the application of the blue laser beam to the phosphor 44, fluorescence is emitted from the phosphor 44. Apart of the blue laser beam is transmitted through the phosphor 44 directly. The violaceous laser beam is transmitted through the phosphor 44 without exciting the phosphor 44. Light emitted from the phosphor 44 is applied to the specimen through the illumination lens 45.

Figure 3A:
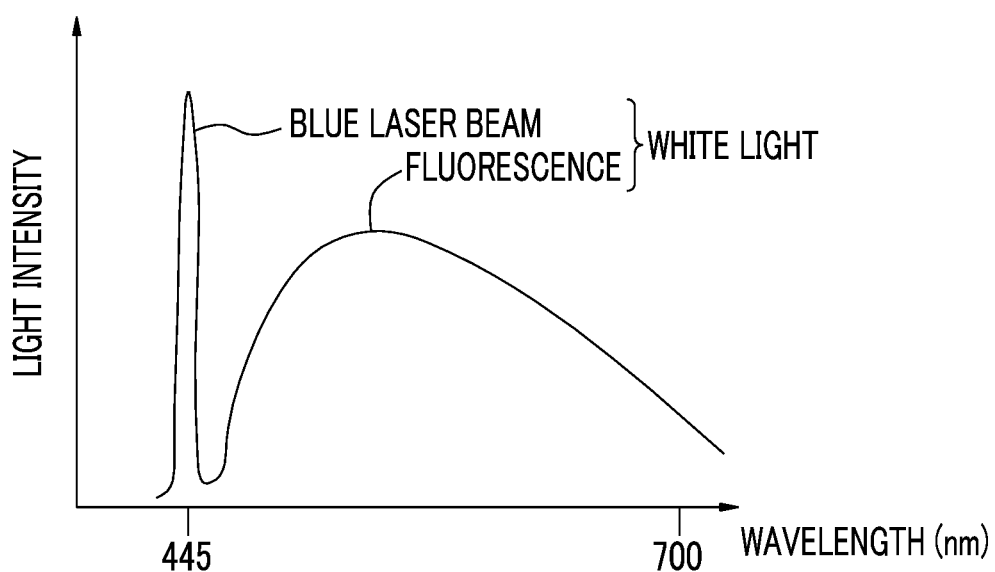
FIG. 3A is a graph showing spectral intensity of white light.
Figure 3B:
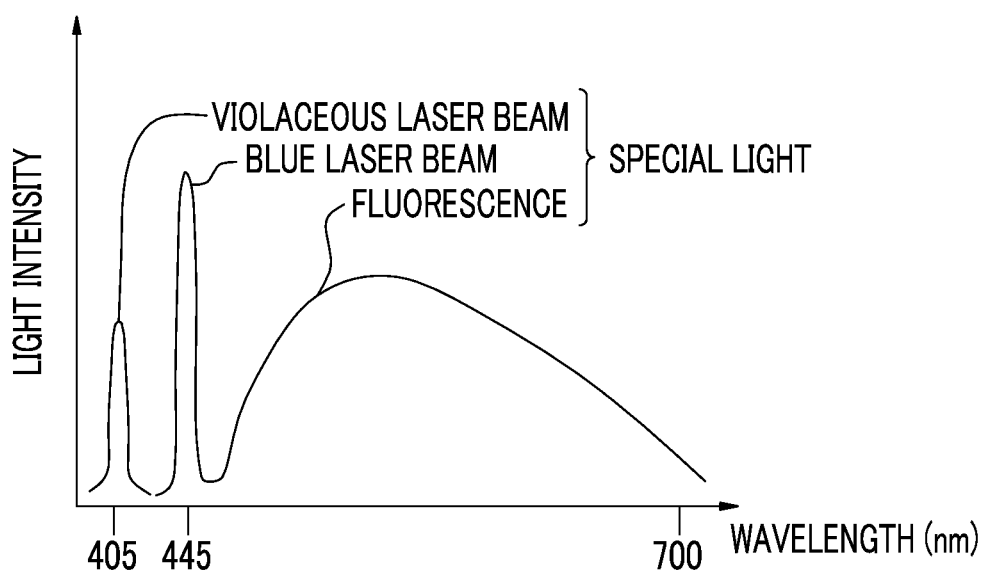
FIG. 3B is a graph showing spectral intensity of special light.

In the normal observation mode, since the blue laser beam primarily enters the phosphor 44, as shown in FIG. 3A, white light which is a combination of the blue laser beam and the fluorescence emitted from the phosphor 44 excited by the blue laser beam is applied to the specimen. In the special observation mode, since both of the violaceous laser beam and the blue laser beam enter the phosphor 44, as shown in FIG. 3B, special light which is a combination of the violaceous laser beam, the blue laser beam, and the fluorescence emitted from the phosphor 44 excited by the blue laser beam is applied to the specimen. In the special observation mode, since the violaceous laser beam is contained in a blue component in addition to the blue laser beam with high light emission intensity, special light contains a high proportion of a blue component, and the wavelength range of special light extends substantially over the entire visible area.

For the phosphor 44, it is preferable to use a phosphor which includes a plurality of phosphors (for example, a YAG-based phosphor or a phosphor, such as BAM (BaMgAl$_{10}$O$_{17}$)) absorbing a part of the blue laser beam and excites and emits green to yellow. As in this configuration example, if a semiconductor light emitting element is used as an excitation light source of the phosphor 44, white light with high intensity is obtained with high light emission efficiency, the intensity of white light can be easily adjusted, and the color temperature or change in chromaticity of white light can be reduced to a low level.

As shown in FIG. 2, the imaging optical system 24b of the endoscope 12 has an imaging lens 46, a zooming lens 47, and a sensor 48. Reflected light from the specimen enters the sensor 48 through the imaging lens 46 and the zooming lens 47. With this, a reflected image of the specimen is formed on the sensor 48. The zooming lens 47 is moved between a telescopic end and a wide end by operating the zoom operation portion 22c. If the zooming lens 47 moves to the telescopic end side, the reflected image of the specimen is enlarged, and if the zooming lens 47 moves to the wide end, the reflected image of the specimen is reduced.

The sensor 48 is a color imaging element, and captures the reflected image of the specimen to output an image signal. It is preferable that the sensor 48 is a charge coupled device (CCD) image sensor, a complementary metal-oxide semiconductor (CMOS) image sensor, or the like. An image sensor used in the invention is an RGB image sensor which has RGB ch with RGB color filters on an imaging surface, and with photoelectric conversion in the respective ch, an R image signal is output from an R pixel with an R (red) color filter, a G image signal is output from a G pixel with the G (green) color filter, and a B image signal is output from a B pixel with the B (blue) color filter.

The sensor 48 may be a so-called complementary color image sensor which comprises C (cyan), M (magenta), Y (yellow), and G (green) color filters on an imaging surface. In a case of the complementary color image sensor, image signals of three colors of RGB can be obtained by color conversion from image signals of four colors of CMYG. In this case, it is necessary to provide means for color-converting the image signals of the three colors of RGB from the image signals of the four colors of CMYG in any of the endoscope 12, the light source device 14, and the processor device 16.

The image signals output from the sensor 48 are transmitted to a CDS/AGC circuit 50. The CDS/AGC circuit 50 performs correlated double sampling (CDS) or automatic gain control (AGC) on the image signals being an analog signal. The image signals having passed through the CDS/AGC circuit 50 are subjected to gamma conversion in a gamma conversion unit 51. With this, image signals having gradations suitable for an output device, such as the monitor 18, are obtained. The image signals after gamma conversion are converted to digital image signals by an A/D converter 52. The A/D-converted digital image signals are input to the processor device 16.

The processor device 16 primarily functions as an image processing device, and comprises a reception unit 54, an image processing switching unit 60, a normal image processing unit 62, a special image processing unit 64, and a video signal generation unit 66. The reception unit 54 functions as an image signal input unit which receives the digital image signals from the endoscope 12 and inputs the digital image signals to the processor device 16. The reception unit 54 comprises a digital signal processor (DSP) 56 and a noise elimination unit 58. The DSP 56 performs gamma correction and color correction processing on the digital image signals. The noise elimination unit 58 performs noise elimination processing (for example, a moving average method, a median filter method, or the like) on the digital image signals subjected to gamma correction or the like in the DSP 56 to eliminate noise from the digital image signals. The noise-eliminated digital image signals are transmitted to the image processing switching unit 60.

The image processing switching unit 60 transits the digital image signals to the normal image processing unit 62 in a case where the normal observation mode is set by the mode selection SW 22b, and transmits the digital image signals to the special image processing unit 64 in a case where the special observation mode is set.

The normal image processing unit 62 performs color conversion processing, color enhancement processing, and structure enhancement processing on the RGB image signals. In the color conversion processing, the digital RGB image signals are subjected to 3×3 matrix processing, gradation conversion processing, three-dimensional LUT processing, or the like and are converted to RGB image signals subjected to the color conversion processing. Next, the RGB image signals subjected to color conversion are subjected to various kinds of color enhancement processing. The RGB image signals subjected to the color enhancement processing are subjected to structure enhancement processing, such as spatial frequency enhancement. The RGB image signals subjected to the structure enhancement processing are input from the normal image processing unit 62 to the video signal generation unit 66.

The special image processing unit 64 enhances the color of an abnormal part changed in color with a lesion, such as atrophy of the stomach, due to atrophic gastritis based on the RGB image signals to generate a special image, in which the structure of the abnormal part is enhanced. The details of the special image processing unit 64 will be described below. The RGB image signals of the generated special image are input from the special image processing unit 64 to the video signal generation unit 66.

The video signal generation unit 66 converts the RGB image signals input from the normal image processing unit 62 or the special image processing unit 64 to a video signal for display as a displayable image on the monitor 18. The monitor 18 displays a normal image or a special image based on the video signal.

Figure 4:
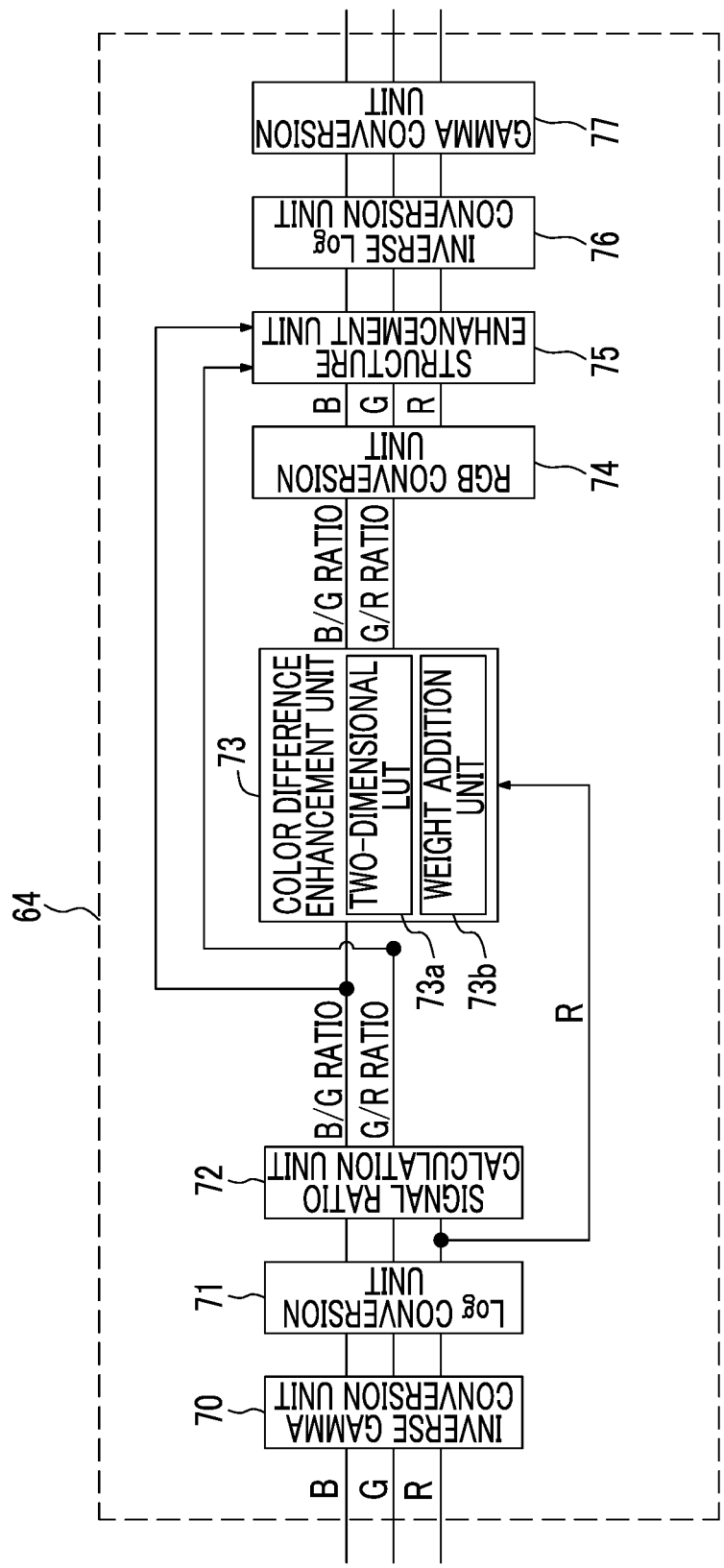
FIG. 4 is a block diagram showing the functions of a special image processing unit.

As shown in FIG. 4, the special image processing unit 64 comprises an inverse gamma conversion unit 70, a Log conversion unit 71, a signal ratio calculation unit 72, a color difference enhancement unit 73, an RGB conversion unit 74, a structure enhancement unit 75, an inverse Log conversion unit 76, and a gamma conversion unit 77. The inverse gamma conversion unit 70 subjects the input digital image signals of RGB three channels to inverse gamma conversion. Since the RGB image signals after inverse gamma conversion are reflectance linear RGB signals which are linear with respect to reflectance from the specimen, the ratio of a signal associated with various kinds of biological information (in this embodiment, information relating to atrophy of the stomach, such a change in color with atrophic gastritis) of the specimen among the RGB image signals is high.

The Log conversion unit subjects the reflectance linear RGB image signals to Log conversion. With this, an R image signal (log R) subjected to Log conversion, a G image signal (log G) subjected to Log conversion, and a B image signal (log B) subjected to Log conversion are obtained. The signal ratio calculation unit 72 performs difference processing (log G−log B=log G/B=−log(B/G)) on the G image signal and the B image signal subjected to Log conversion to calculate the B/G ratio (a portion except for "−log" in −log(B/G) is represented as "B/G ratio"). The "B/G ratio" represents a portion except for "−log" in −log(B/G). Difference processing (log R−log G=log R/G=−log(G/R)) is performed based on the R image signal and the G image signal subjected to Log conversion to calculate the G/R ratio. Similarly to the B/G ratio, the G/R ratio represents a portion except for "−log" in −log(G/R).

Figure 5:
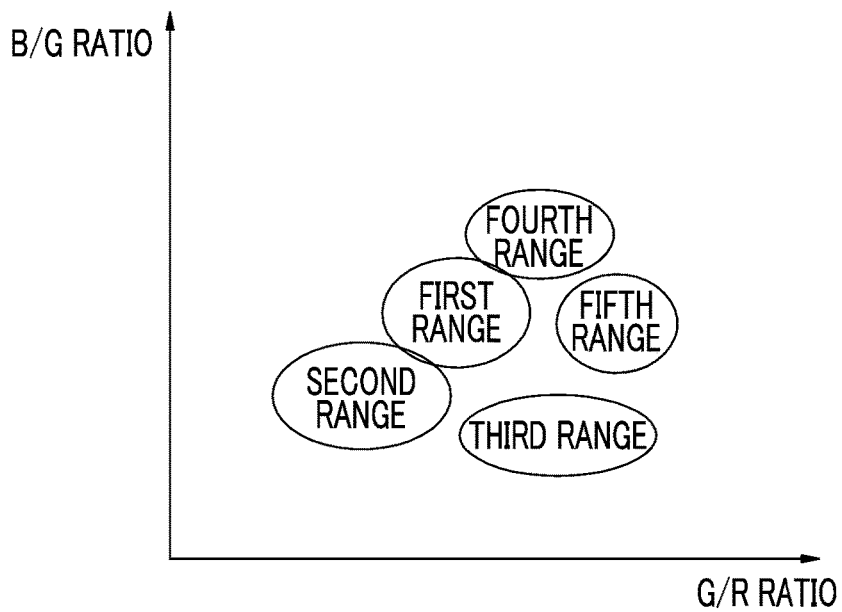
FIG. 5 is a graph showing the positional relationship of first to fifth ranges.

The color difference enhancement unit 73 expands the difference between the B/G ratio and the G/R ratio in the first range and the B/G ratio and the G/R ratio in each of the second to fifth ranges in a two-dimensional space (corresponding to a "feature space" of the invention) of a B/G ratio and a G/R ratio shown in FIG. 5 to enhance the color difference between a normal part and an abnormal part (an atrophic mucosa area, a deep blood vessel area, a brownish area (BA), or reddened area) on an observation area.

Figure 6:
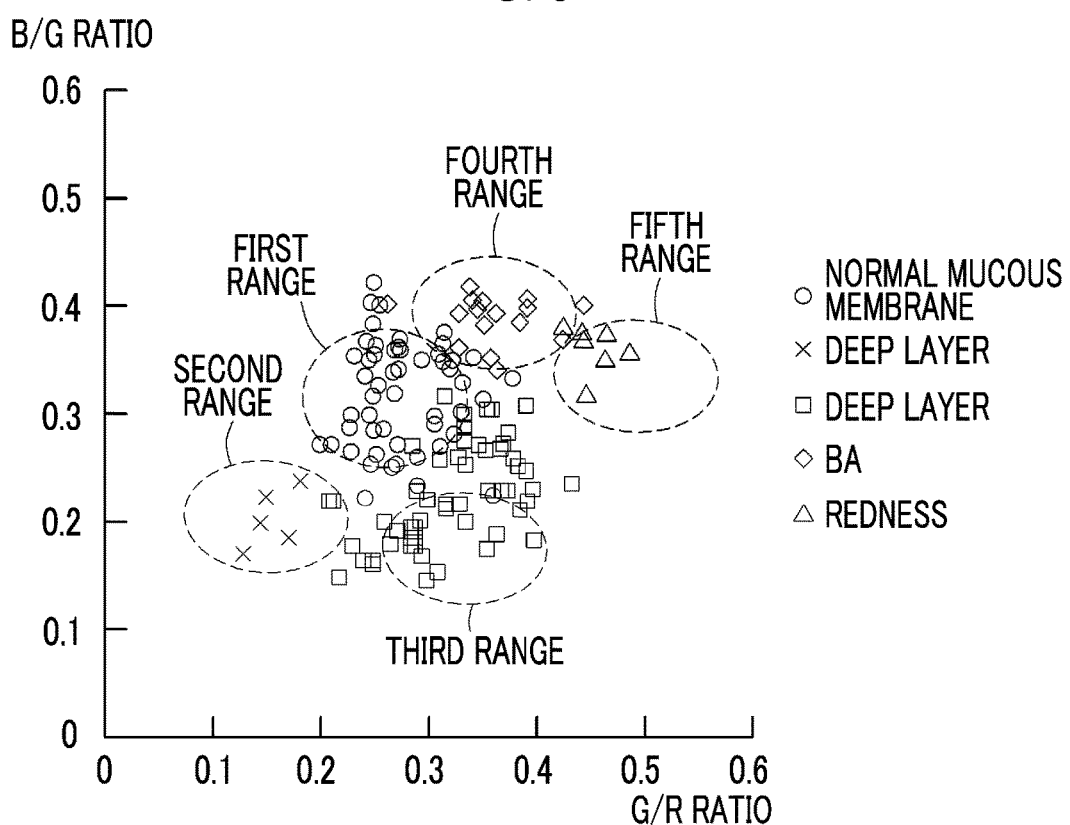
FIG. 6 is a graph showing measured data which indicates the distribution of a B/G ratio and a G/R ratio obtained at the time of illumination with special light (the light emission intensity of a blue laser beam is higher than the light emission intensity of a violaceous laser beam)

As indicated by measured data of FIG. 6, the first range includes a lot of the B/G ratio and the G/R ratio of a portion where there is a normal part, such as a normal mucosa (in FIG. 6, a normal mucosa is represented to by "○"), and the first range is positioned at the substantially center on the two-dimensional space. The second range includes a lot of the B/G ratio and the G/R ratio of a portion where there is an atrophic mucosa (in FIG. 6, an atrophic mucosa is represented by "x"), and the second range is positioned on the obliquely upper left side of the first range on the two-dimensional space. In a case where the relationship between the first range and the second range is defined in terms of hue and saturation, the first range and the second range have the same hue, and the second range has saturation lower than that in the first range.

The third range includes a lot of the B/G ratio and the G/R ratio of a portion where there is a deep blood vessel (in FIG. 6, a deep blood vessel is represented by "□"), and the third range is positioned on the obliquely lower right side of the first range. In a case where the relationship between the first range and the third range is defined in terms of hue and saturation, the first range and the third range have the same saturation and have different hues. The fourth range includes a lot of the B/G ratio and the G/R ratio of a portion where there is a BA (in FIG. 6, a BA is represented by "◇"), and the fourth range is positioned on the obliquely upper right side of the first range. The fifth range includes a lot of the B/G ratio and G/R ratio of a portion where there is reddened area (in FIG. 6, reddened area is represented by "Δ"), and the fifth range is positioned on the right side of the first range.

The color difference enhancement unit 73 comprises a two-dimensional LUT 73a and a weighting addition unit 73b. The two-dimensional LUT 73a stores the B/G ratio and the G/R ratio of each of the second to fifth ranges in association with color difference enhancement amounts for use in expanding the color difference between the B/G ratio and the G/R ratio of each of the second to fourth ranges and the B/G ratio and the G/R ratio of the first range. In the two-dimensional LUT 73a, the color difference enhancement amounts $\Delta^*$(B/G ratio) and $\Delta^*$(G/R ratio) of the second range associated with the B/G ratio and the G/R ratio of the second range are obtained by color difference enhancement amount calculation processing for the second range based on the B/G ratio and the G/R ratio of the second range.

The color difference enhancement amounts $\Delta^{}$(B/G ratio) and $\Delta^{}$(G/R ratio) of the third range associated with the B/G ratio and the G/R ratio of the third range are obtained by color difference enhancement amount calculation processing for the third range based on the B/G ratio and the G/R ratio of the third range. The color difference enhancement amounts $\Delta^{*}$(B/G ratio) and $\Delta^{*}$(G/R ratio) of the fourth range associated with the B/G ratio and the G/R ratio of the fourth range are obtained by color different enhancement amount calculation processing for the fourth range based on the B/G ratio and the G/R ratio of the fourth range. The color difference enhancement amounts $\Delta^{*4}$(B/G ratio) and $\Delta^{*4}$(G/R ratio) for the fifth range associated with the B/G ratio and the G/R ratio of the fifth range are obtained by color different enhancement amount calculation processing for the fifth range based on the B/G ratio and the G/R ratio of the fifth range. Since color difference expansion is not performed for the B/G ratio and the G/R ratio (including the B/G ratio and the G/R ratio of the first range) of an unenhanced range other than the B/G ratio and the G/R ratio of each of the second to fifth ranges, the B/G ratio and the G/R ratio of the unenhanced range is stored in the two-dimensional LUT 73a in associated with a color difference enhancement amount "0".

The color different enhancement amount calculation processing for each of the second to fifth ranges is performed by the following procedure. The color different enhancement amount calculation processing for the second range includes first range average value calculation processing, polar coordinate conversion processing, radius vector difference expansion processing, quadrature coordinate conversion processing, and difference processing. First, the average values of the B/G ratio and the G/R ratio in the first range are calculated by the first range average value calculation processing. Next, the average values of the B/G ratio and the G/R ratio in the first range are subjected to polar coordinate conversion by the polar coordinate conversion processing to obtain a first range average value (rm,θm) subjected to polar coordinate conversion. Furthermore, the B/G ratio and the G/R ratio in the second range are subjected to polar coordinate conversion to obtain a second range signal (ri,θi) subjected to polar coordinate conversion.

Figure 7:
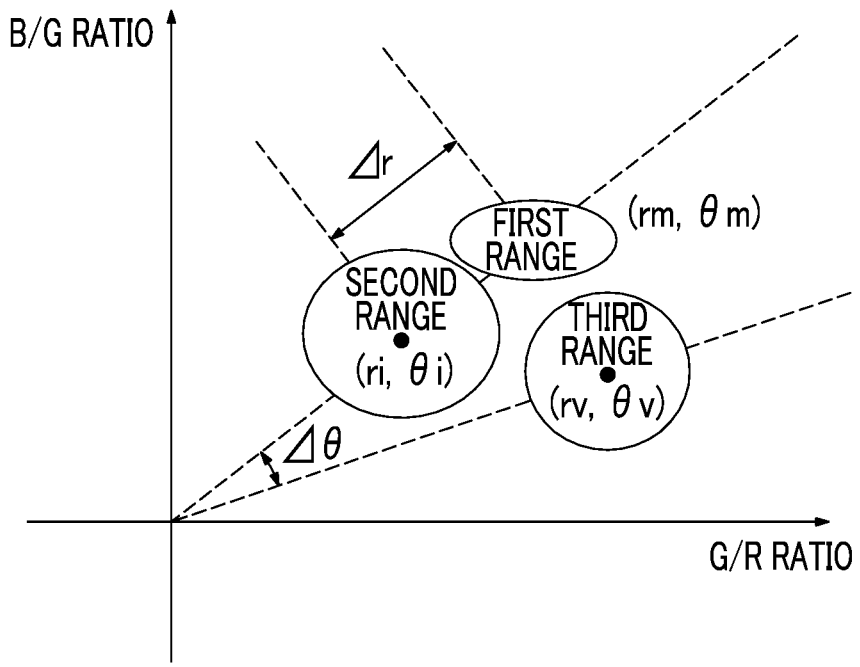
FIG. 7 is an explanatory view showing the positions of a second range and a third range before radius vector difference or deflection angle difference expansion in a two-dimensional space (B/G ratio, G/R ratio)
Figure 8:
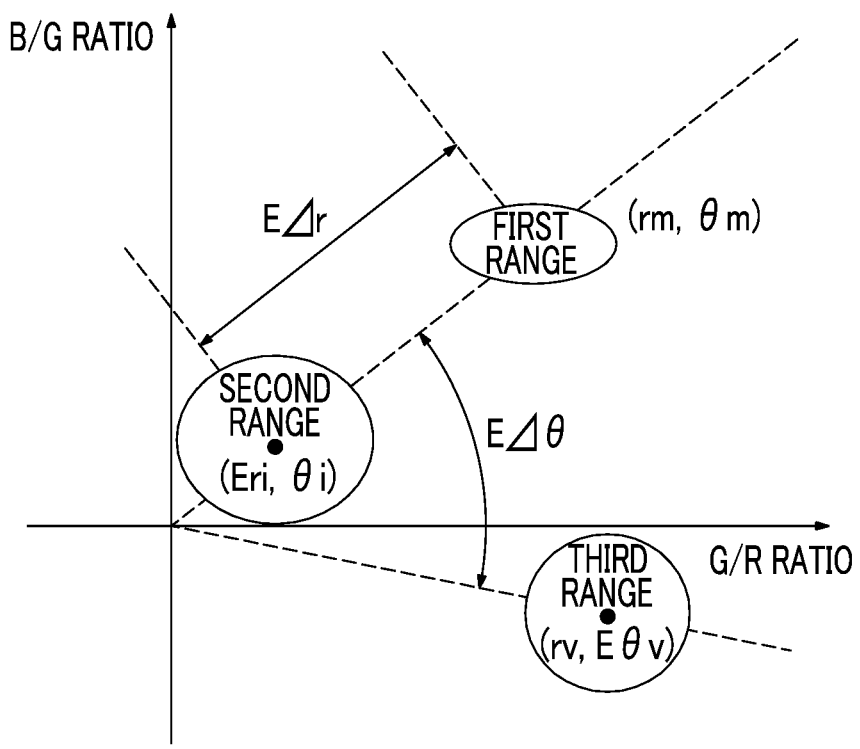
FIG. 8 is an explanatory view showing the positions of the second range and the third range after radius vector difference or deflection angle difference expansion in the two-dimensional space (B/G ratio, G/R ratio)

Next, as shown in FIG. 7, the radius vector difference Δr between the first range average value (rm,θm) and the second range signal (ri,θi) subjected to polar coordinate conversion is expanded by the radius vector difference expansion processing. The radius vector difference expansion processing is performed by Expression (1-1) described below. With this, a second range signal (Eri,θi) subjected to radius vector difference expansion shown in FIG. 8 is obtained. The radius vector difference between the second range signal (Eri,θi) subjected to radius vector difference expansion and the first range average value (rm,θm) is EΔr greater than Δr.

$$Eri=(ri-rm)\cdot\alpha+rm \text{ (where } \alpha\geq1\text{)} \quad (1\text{-}1):$$

Next, the second range signal (Eri,θi) subjected to radius vector difference expansion is converted to quadrature coordinates by the quadrature coordinate conversion processing. With this, the B/G ratio and the G/R ratio of the second range subjected to radius vector difference expansion are obtained. Next, as shown in (1-2) and (1-3), the difference processing between the B/G ratio and the G/R ratio of the second range subjected to radius vector difference expansion and the B/G ratio and the G/R ratio of the second range before radius vector difference expansion is performed to calculate color different expansion amounts Δ*(B/G ratio) and Δ*(G/R ratio) of the second range.

Δ*(B/G ratio)=|the B/G ratio of the second range
subjected to radius vector difference expansion–
the B/G ratio of the second range before radius
vector difference expansion| (1-2)

Δ*(G/R ratio)=|the G/R ratio of the second range
subjected to radius vector difference expansion–
the G/R ratio of the second range before radius
vector difference expansion (1-3)

Figure 9:
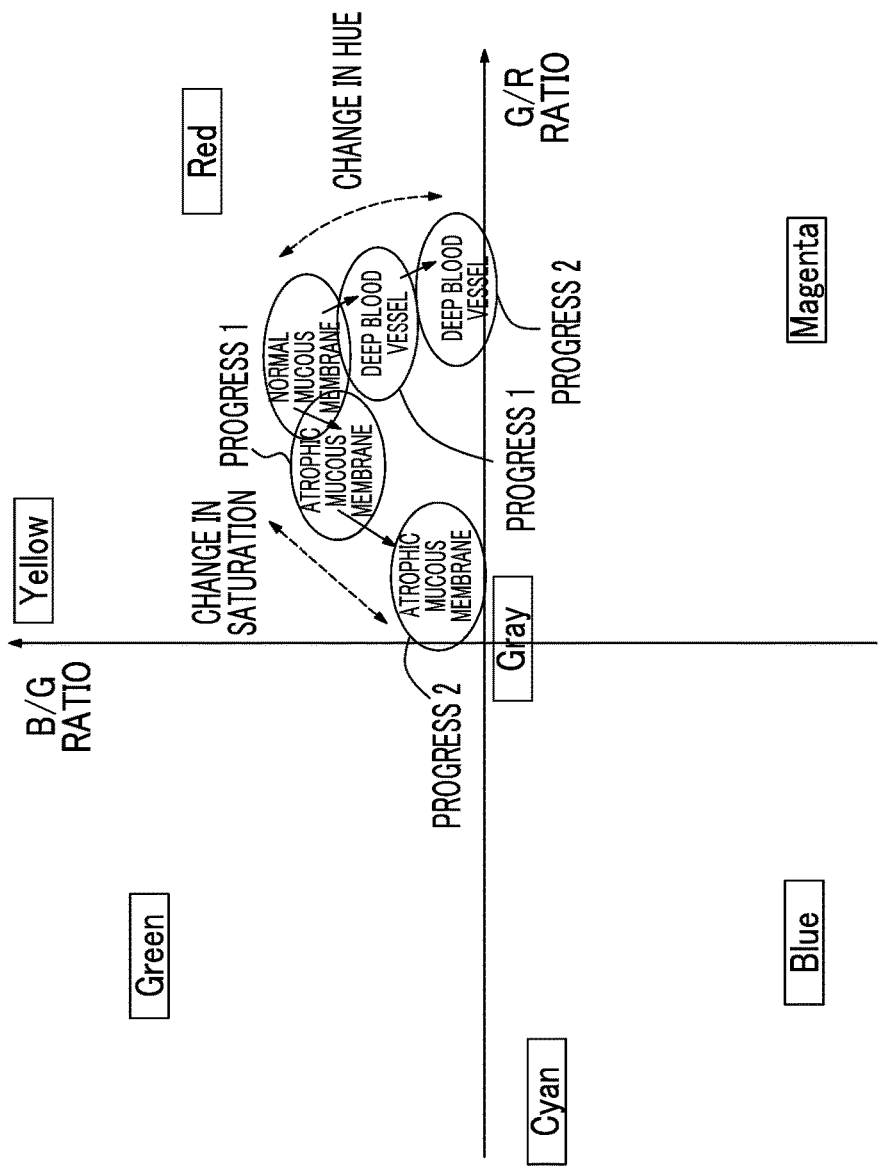
FIG. 9 is an explanatory view for use in describing the relationship between a two-dimensional space (B/G ratio, G/R ratio) and chromaticity, and change in the distribution of a B/G ratio and a G/R ratio with the progress of atrophic gastritis.

As shown in FIGS. 7 and 8, the radius vector difference expansion processing of the second range expands the radius vector difference Δr in a decreasing direction of saturation in a state where the hue is maintained. Change in color due to the expansion processing matches change in color of a faded atrophic mucosa shown in FIG. 9 with the progress of atrophic gastritis. In FIG. 9, Progress 2 shows that atrophic gastritis is progressing more than Progress 1, and it is understood that, in a case of Progress 1, the difference between an atrophic mucosa area and a normal mucosa area is small; however, in a case of Progress 2, the hue is substantially maintained as it is, and only saturation is lowered, and accordingly, the difference between the atrophic mucosa area and the normal mucosa area is great.

In a case of further enhancing the difference in color of the normal mucosa area and the atrophic mucosa area, not only expansion in a saturation direction (expansion of the radius vector difference) but also expansion in a hue direction (expansion of the deflection angle difference) may be performed. In a case where atrophy is progressing to a high level, if the value of α of Expression (1-1) is too great, since the color of the atrophic mucosa area is bluish, in this case, the value of a is decreased (adjusted by operation with the console 20), whereby the color of the atrophic mucosa area can match the actual color (faded color) of the atrophic mucosa.

The color different enhancement amount calculation processing for the third range includes first range average value calculation processing, polar coordinate conversion processing, deflection angle difference expansion processing, quadrature coordinate conversion processing, and difference processing. First, the average values of the B/G ratio and the G/R ratio in the first range are calculated by the first range average value calculation processing. Next, the average values of the B/G ratio and the G/R ratio in the first range are subjected to polar coordinate conversion by the polar coordinate conversion processing to obtain a first range average value (rm,θm) subjected to polar coordinate conversion. The B/G ratio and the G/R ratio in the third range are subjected to polar coordinate conversion to obtain a third range signal (rv,θv) subjected to polar coordinate conversion.

Next, as shown in FIG. 7, the deflection angle difference Δθ between the first range average value (rm,θm) and the third range signal (rv,θv) subjected to polar coordinate conversion is expanded by the deflection angle difference expansion processing. The deflection angle difference expansion processing is performed by Expression (2-1) described below. With this, a third range signal (Erv,θv) subjected to deflection angle difference expansion shown in FIG. 8 is obtained. The deflection angle difference between the third range signal (Erv,θv) subjected to deflection angle difference expansion and the first range average value (rm, θm) is EΔθ greater than Δθ.

$$E\theta v=(\theta v-\theta m)\cdot\beta+\theta m \text{ (where } \beta\geq1\text{)} \quad (2\text{-}1):$$

Next, the third range signal (Erv,θv) subjected to deflection angle difference expansion is converted to quadrature coordinates by the quadrature coordinate conversion processing. With this, the B/G ratio and the G/R ratio of the third range subjected to deflection angle difference expansion are obtained. Next, as shown in Expressions (2-2) and (2-3) described below, the difference processing between the B/G ratio and the G/R ratio of the third range subjected to deflection angle difference expansion and the B/G ratio and the G/R ratio of the third range before deflection angle difference expansion is performed to calculate color difference expansion amounts Δ(B/G ratio) and Δ(G/R ratio) of the third range.

Δ**(B/G ratio)=|the B/G ratio of the third range subjected to deflection angle difference expansion–
the B/G ratio of the third range before deflection angle difference expansion| (2-2)

$$\Delta^{**}(G/R \text{ ratio}) = |\text{the } G/R \text{ ratio of the third range subjected to deflection angle difference expansion} - \text{the } G/R \text{ ratio of the third range before deflection angle difference expansion}| \quad (2\text{-}3)$$

As shown in FIGS. 7 and 8, the deflection angle difference expansion processing of the third range expands the deflection angle difference $\Delta\theta$ in a hue direction in a state where saturation is maintained. As shown in FIG. 9, change in color due to the expansion processing matches change in color of a deep blood vessel being actualized with the progress of atrophic gastritis. In FIG. 9, Progress 2 shows that atrophic gastritis is progressing more than Progress 1, and it is understood that, in Progress 1, the difference between the deep blood vessel area and the normal mucosa area is small; however, in a case of Progress 2, saturation is substantially maintained as it is and only a hue is changed, and accordingly, the difference between the deep blood vessel area and the normal mucosa area is great.

In a case of further enhancing the difference between the normal mucosa area and the deep blood vessel area, not only expansion in a hue direction (expansion of the deflection angle difference) but also expansion in a saturation direction (expansion of the radius vector difference) may be performed. In a case where atrophy is progressing to a high level, if the value of $\beta$ of Expression (2-1) is too great, since the color of the deep blood vessel area has a magenta tone, in this case, the value of $\beta$ is decreased (adjusted by operation with the console 20), whereby the color of the deep blood vessel area can match the color of the deep blood vessel.

The color different enhancement amount calculation processing for the fourth range includes first range average value calculation processing, polar coordinate conversion processing, radius vector difference and deflection angle difference expansion processing, quadrature coordinate conversion processing, and difference processing. First, the average values of the B/G ratio and the G/R ratio in the first range are calculated by the first range average value calculation processing. Next, the average values of the B/G ratio and the G/R ratio in the first range are subjected to polar coordinate conversion by the polar coordinate conversion processing to obtain a first range average value (rm,θm) subjected to polar coordinate conversion. The B/G ratio and the G/R ratio in the fourth range are subjected to polar coordinate conversion to obtain a fourth range signal (rk,θk) subjected to polar coordinate conversion.

Next, the radius vector difference $\Delta r$ and the deflection angle difference $\Delta\theta$ between the first range average value (rm,θm) and the fourth range signal (rk,θk) subjected to polar coordinate conversion are expanded by the radius vector difference and deflection angle difference expansion processing. The radius vector difference and deflection angle difference expansion processing is performed by Expressions (3-1) and (3-2) described below. With this, a fourth range signal (Erk,Eθk) subjected to radius vector difference and deflection angle difference expansion, in which both of the radius vector difference $\Delta r$ and the deflection angle difference $\Delta\theta$ are expanded, is obtained.

$$Erk = (rk - rm) \cdot \alpha + rm \text{ (where } \alpha \geq 1\text{)} \quad (3\text{-}1):$$

$$E\theta k = (\theta k - \theta m) \cdot \beta + \theta m \text{ (where } \beta \geq 1\text{)} \quad (3\text{-}2):$$

Next, the fourth range signal (Erv,θv) subjected to radius vector difference and deflection angle difference expansion is converted to quadrature coordinates by the quadrature coordinate conversion processing. With this, the B/G ratio and the G/R ratio of the fourth range subjected to radius vector difference and deflection angle difference expansion are obtained. Next, as shown in Expressions (3-3) and (3-4) described below, the difference processing between the B/G ratio and the G/R ratio of the fourth range subjected to radius vector difference and deflection angle difference expansion and the B/G ratio and the G/R ratio of the fourth range before radius vector difference and deflection angle difference expansion is performed to calculate color difference expansion amounts $\Delta^{*}(B/G \text{ ratio})$ and $\Delta^{*}(G/R \text{ ratio})$ of the fourth range.

$$\Delta^{***}(B/G \text{ ratio}) = |\text{the } B/G \text{ ratio of the fourth range subjected to radius vector difference and deflection angle difference expansion} - \text{the } B/G \text{ ratio of the fourth range before radius vector difference and deflection angle difference expansion}| \quad (3\text{-}3)$$

$$\Delta^{***}(G/R \text{ ratio}) = |\text{the } G/R \text{ ratio of the fourth range subjected to radius vector difference and deflection angle difference expansion} - \text{the } G/R \text{ ratio of the fourth range before radius vector difference and deflection angle difference expansion}| \quad (3\text{-}4)$$

The color different enhancement amount calculation processing for the fifth range includes first range average value calculation processing, polar coordinate conversion processing, radius vector difference and deflection angle difference expansion processing, quadrature coordinate conversion processing, and difference processing. First, the average values of the B/G ratio and the G/R ratio in the first range are calculated by the first range average value calculation processing. Next, the average values of the B/G ratio and the G/R ratio in the first range are subjected to polar coordinate conversion by the polar coordinate conversion processing to obtain a first range average value (rm,θm) subjected to polar coordinate conversion. The B/G ratio and the G/R ratio in the fifth range are subjected to polar coordinate conversion to obtain a fifth range signal (rp,θp) subjected to polar coordinate conversion.

Next, the radius vector difference $\Delta r$ and the deflection angle difference $\Delta\theta$ between the first range average value (rm,θm) and the fifth range signal (rp,θp) subjected to polar coordinate conversion are expanded by the radius vector difference and deflection angle difference expansion processing. The radius vector difference and deflection angle difference expansion processing is performed by Expressions (4-1) and (4-2) described below. With this, a fifth range signal (Erp,Eθp) subjected to radius vector difference and deflection angle difference expansion, in which both of the radius vector difference $\Delta r$ and the deflection angle difference $\Delta\theta$ are expanded, is obtained.

$$Erp = (rp - rm) \cdot \alpha + rm \text{ (where } \alpha \geq 1\text{)} \quad (4\text{-}1):$$

$$E\theta p = (\theta p - \theta m) \cdot \beta + \theta m \text{ (where } \beta \geq 1\text{)} \quad (4\text{-}2):$$

Next, the fifth range signal (Erp,θp) subjected to radius vector difference and deflection angle difference expansion is converted to quadrature coordinates by the quadrature coordinate conversion processing. With this, the B/G ratio and the G/R ratio of the fifth range subjected to radius vector difference and deflection angle difference expansion are obtained. Next, as shown in Expressions (4-3) and (4-4) described below, the difference processing between the B/G ratio and the G/R ratio of the fifth range subjected to radius vector difference and deflection angle difference expansion and the B/G ratio and the G/R ratio of the fifth range before radius vector difference and deflection angle difference expansion is performed to calculate color difference expansion amounts $\Delta^{*4}(B/G \text{ ratio})$ and $\Delta^{*4}(G/R \text{ ratio})$ of the fifth range.

$\Delta^{*4}(B/G\ \text{ratio}) = |\text{the}\ B/G\ \text{ratio of the fifth range subjected to radius vector difference and deflection angle difference expansion–the}\ B/G\ \text{ratio of the fifth range before radius vector difference and deflection angle difference expansion}|$  (4-3)

$\Delta^{*4}(G/R\ \text{ratio}) = |\text{the}\ G/R\ \text{ratio of the fifth range subjected to radius vector difference and deflection angle difference expansion–the}\ G/R\ \text{ratio of the fifth range before radius vector difference and deflection angle difference expansion}|$  (4-4)

The weighting addition unit 73b specifies the color difference enhancement amounts corresponding to the B/G ratio and the G/R ratio determined by the signal ratio calculation unit 72 with reference to the two-dimensional LUT 73a. The weighting addition unit 73b calculates an enhancement coefficient f(R) which is multiplied to the color difference enhancement amounts based on the R image signal (log R) subjected to Log conversion. The R image signal includes a lot of signals corresponding to light reflected from an observation target without being absorbed in the observation target, compared to the B image signal or the G image signal of other colors. Accordingly, it is possible to understand the amount of reflected light from the R image signal.

Figure 10:
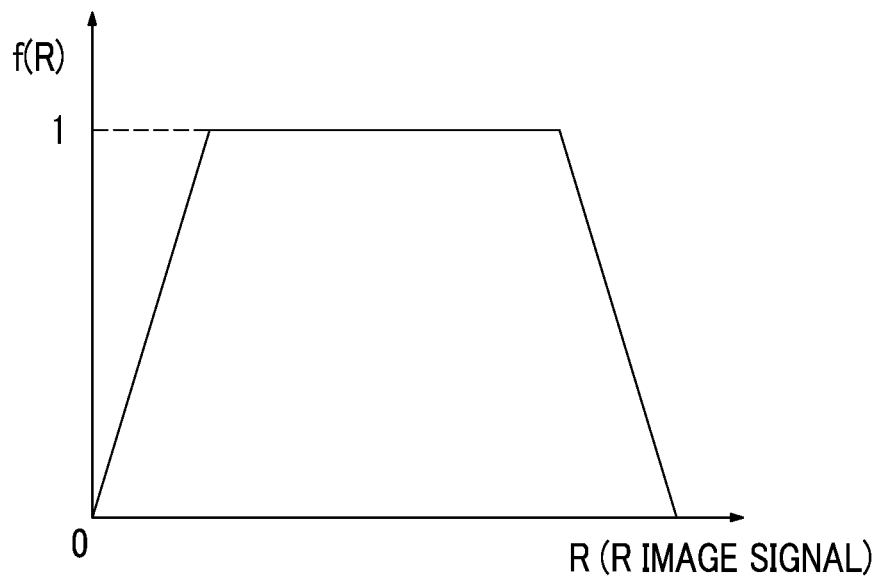
FIG. 10 is a graph showing the relationship between an R image signal and an enhancement coefficient f(R)

As shown in FIG. 10, in a case where the R image signal subjected to Log conversion falls within a given range, the enhancement coefficient f(R) is set to "1". In a case where the R image signal subjected to Log conversion exceeds an upper limit value or falls below a lower limit value, the enhancement coefficient f(R) is set to be smaller than "1". When the R image signal subjected to Log conversion which exceeds the upper limit value is increased, or when the R image signal subjected to Log conversion which falls below the lower limit value is decreased, the enhancement coefficient is set small. In this way, the enhancement coefficient of a high luminance portion where the R image signal exceeds the upper limit value or a low luminance portion where the R image signal falls below the lower limit value is decreased to decrease the color difference enhancement amount, whereby it is possible to suppress enhancement of halation or the like.

The weighting addition unit 73b performs weighting addition processing on the B/G ratio and the G/R ratio based on the specified color difference enhancement amounts and the calculated enhancement coefficient. In a case where the color difference enhancement amounts $\Delta^*(B/G\ \text{ratio})$ and $\Delta^*(G/R\ \text{ratio})$ corresponding to the B/G ratio and the G/R ratio of the second range are specified in the two-dimensional LUT 73a, weighting addition processing by Expression (4) described below is performed. With this, the B/G ratio and the G/R ratio of the second range subjected to color difference enhancement are obtained.

the B/G ratio and the G/R ratio of the second range subjected to color difference enhancement=the B/G ratio and the G/R ratio of the second range+$\Delta^*(B/G\ \text{ratio})$ and $\Delta^*(G/R\ \text{ratio}) \times f(R)$  (4):

In a case where display is performed on the monitor 18 based on the B/G ratio and the G/R ratio of the second range subjected to color difference enhancement, a color difference-enhanced image in which the atrophic mucosa area is displayed clearly in a color different from the normal mucosa area and the color of the atrophic mucosa area is displayed in a color similar to the color of a mucosa at the time of atrophic gastritis is displayed. With this, it is possible to reliably determine the boundary between the normal mucosa area and an area of an atrophic part. The radius vector difference expansion processing is particularly effective in a case where the difference between the normal mucosa area and the atrophic mucosa area is slight (for example, in a case of atrophy included in the group B or the group C in the ABC examination during the progress of atrophy).

In a case where the color difference enhancement amounts $\Delta^{}(B/G\ \text{ratio})$ and $\Delta^{}(G/R\ \text{ratio})$ corresponding to the B/G ratio and the G/R ratio of the third range are specified in the two-dimensional LUT 73a, weighting addition processing by Expression (5) described below is performed. With this, the B/G ratio and the G/R ratio of the third range subjected to color difference enhancement are obtained.

the B/G ratio and the G/R ratio of the third range subjected to color difference enhancement=the B/G ratio and the G/R ratio of the third range+$\Delta^{}(B/G\ \text{ratio})$ and $\Delta^{}(G/R\ \text{ratio}) \times f(R)$  (5):

In a case where display is performed on the monitor 18 based on the B/G ratio and the G/R ratio of the third range subjected to color difference enhancement, a color difference-enhanced image in which the deep blood vessel area is displayed clearly in a color different from the normal mucosa area and the deep blood vessel reliably becomes see-through due to actualization of the color of the deep blood vessel is displayed. With this, it is possible to reliably determine the boundary between the normal mucosa area and the deep blood vessel area. The deflection angle difference expansion processing is particularly effective in a case where the deep blood vessel does not become so see-through (for example, in a case of atrophy included in the group B or the group C in the ABC examination during the progress of atrophy).

In a case where the color difference enhancement amounts $\Delta^{*}(B/G\ \text{ratio})$ and $\Delta^{*}(G/R\ \text{ratio})$ corresponding to the B/G ratio and the G/R ratio of the fourth range are specified in the two-dimensional LUT 73a, weighting addition processing by Expression (6-1) described below is performed. With this, the B/G ratio and the G/R ratio of the fourth range subjected to color difference enhancement are obtained.

the B/G ratio and the G/R ratio of the fourth range subjected to color difference enhancement=the B/G ratio and the G/R ratio of the fourth range+$\Delta^{*}(B/G\ \text{ratio})$ and $\Delta^{*}(G/R\ \text{ratio}) \times f(R)$  (6-1):

In a case where display is performed on the monitor 18 based on the B/G ratio and the G/R ratio of the fourth range subjected to color difference enhancement, a color difference-enhanced image in which the BA is displayed clearly in a color different from the normal mucosa area is displayed. With this, it is possible to reliably determine the boundary between the normal mucosa area and the BA.

In a case where the color difference enhancement amounts $\Delta^{*4}(B/G\ \text{ratio})$ and $\Delta^{*4}(G/R\ \text{ratio})$ corresponding to the B/G ratio and the G/R ratio of the fifth range are specified in the two-dimensional LUT 73a, weighting addition processing by Expression (6-2) described below is performed. With this, the B/G ratio and the G/R ratio of the fifth range subjected to color difference enhancement are obtained.

the B/G ratio and the G/R ratio of the fifth range subjected to color difference enhancement=the B/G ratio and the G/R ratio of the fifth range+$\Delta^{*4}(B/G\ \text{ratio})$ and $\Delta^{*4}(G/R\ \text{ratio}) \times f(R)$  (6-2):

In a case where display is performed on the monitor 18 based on the B/G ratio and the G/R ratio of the fifth range subjected to color difference enhancement, a color difference-enhanced image in which the reddened area is displayed clearly in a color different from the normal mucosa area is displayed. With this, it is possible to reliably determine the boundary between the normal mucosa area and the reddened area.

Figure 11:
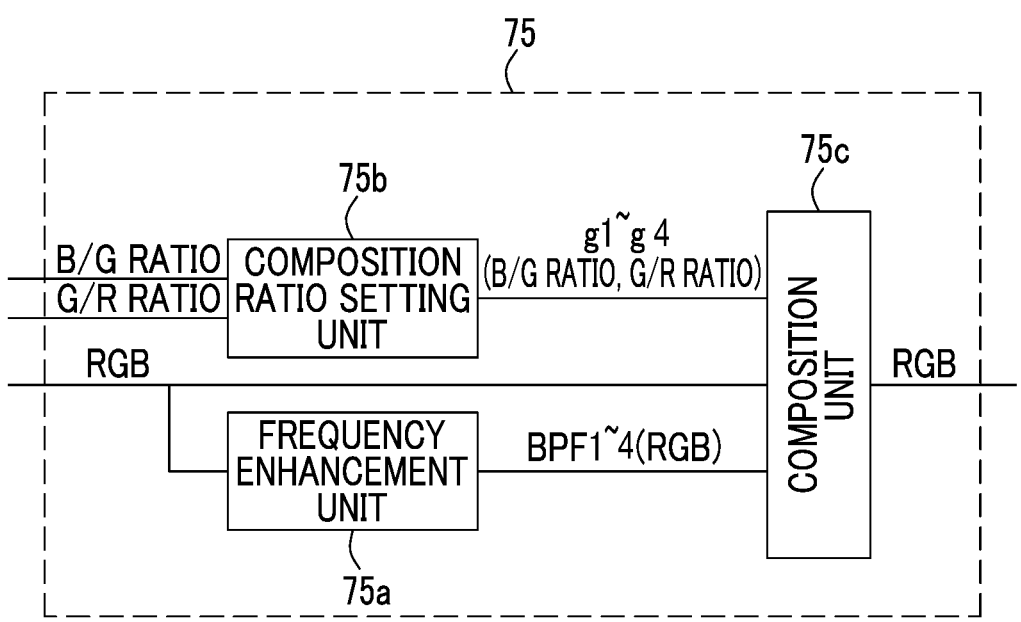
FIG. 11 is a block diagram showing the functions of a structure enhancement unit.

The RGB conversion unit 74 re-converts the B/G ratio and the G/R ratio subjected to color difference enhancement obtained by the color difference enhancement unit 73 to RGB image signals subjected to color difference enhancement. With this, the color difference-enhanced image is obtained from the RGB image signals. The structure enhancement unit 75 performs structure enhancement of the atrophic mucosa area, the deep blood vessel area, the BA, or the reddened area based on the B/G ratio and the G/R ratio before color difference enhancement and the color difference-enhanced image. As shown in FIG. 11, the structure enhancement unit 75 comprises a frequency enhancement unit 75*a*, a composition ratio setting unit 75*b*, and a composition unit 75*c*.

The frequency enhancement unit 75*a* subjects a plurality of kinds of filtering (Band Pass Filtering (BPF)) to the RGB image signals of the saturation-enhanced image to obtain a plurality of frequency-enhanced images. In the frequency enhancement unit 75*a*, frequency filtering for an atrophic mucosa area for extracting a first frequency component having a low frequency including a lot of the atrophic mucosa area, frequency filtering for a deep blood vessel area for extracting a frequency component having a medium frequency including a lot of the second deep blood vessel area, frequency filtering for BA for extracting a third frequency component having a low frequency including a lot of the BA, and frequency filtering for reddened area for extracting a fourth frequency component having a low frequency including a lot of the reddened area are used.

Frequency filtering for an atrophic mucosa area is performed to obtain a first frequency component-enhanced image BPF1 (RGB). Frequency filtering for a deep blood vessel area is performed to obtain a second frequency component-enhanced image BPF2 (RGB). Frequency filtering for a BA is performed to obtain a third frequency component-enhanced image BPF3 (RGB). Frequency filtering for a reddened area is performed to obtain a fourth frequency component-enhanced image BPF4 (RGB).

The composition ratio setting unit 75*b* sets composition ratios g1 (the B/G ratio and the G/R ratio), g2 (the B/G ratio and the G/R ratio), g3 (the B/G ratio and the G/R ratio), and g4 (the B/G ratio and the G/R ratio) representing the ratio for composing the first to fourth frequency component-enhanced images BPF1 (RGB) to BPF4 (RGB) with the RGB image signals of the color difference-enhanced image for respective pixels based on the B/G ratio and the G/R ratio before color difference enhancement. As shown in FIG. 12, for the pixels where the B/G ratio and the G/R ratio are within the second range, the composition ratio g1 (the B/G ratio and the G/R ratio) is set to "100%", and other composition ratios g2, g3, and g4 (the B/G ratio and the G/R ratio) are set to "0%".

For the pixels where the B/G ratio and the G/R ratio are within the third range, the composition ratio g2 (the B/G ratio and the G/R ratio) is set to "100%", and other composition ratios g1, g3, and g4 (the B/G ratio and the G/R ratio) are set to "0%". For the pixels where the B/G ratio and the G/R ratio are within the fourth range, the composition ratio g3 (the B/G ratio and the G/R ratio) is set to "100%", and other composition ratios g1, g2, and g4 (the B/G ratio and the G/R ratio) are set to "0%". For the pixels where the B/G ratio and the G/R ratio are within the fifth range, the composition ratio g4 (the B/G ratio and the G/R ratio) is set to "100%", and other composition ratios g1, g2, and g3 (the B/G ratio and the G/R ratio) are set to "0%". For the pixels where the B/G ratio and the G/R ratio are not within any of the second to fifth ranges, the composition ratios g1 to g4 (the B/G ratio and the G/R ratio) are set to "0%".

The composition unit 75*c* composes the RGB image signals (color difference-enhanced image (RGB)) of the color difference-enhanced image with the first to fourth frequency component-enhanced images BPF1 (RGB) to BPF4 (RGB) at the composition ratios set for the respective pixels by the composition ratio setting unit 75*b* based on Expression (7) described below. With this, a color difference and structure-enhanced image (color difference and structure-enhanced image (RGB)) having the RGB image signals is obtained.

the color difference and structure-enhanced image
($RGB$)=the color difference-enhanced image
($RGB$)+$BPF1(RGB)$×Gain1($RGB$)×g1 (the $B/G$
ratio and the $G/R$ ratio)+$BPF2(RGB)$×Gain2
($RGB$)×g2 (the $B/G$ ratio and the $G/R$ ratio)+
$BPF3(RGB)$×Gain3($RGB$)×g3 (the $B/G$ ratio
and the $G/R$ ratio)+$BPF4(RGB)$×Gain4
($RGB$)×g4 (the $B/G$ ratio and the $G/R$ ratio) (7):

Gain1 (RGB) to Gain4 (RGB) of Expression (7) are determined in advance by the characteristics of the edges of the first to fourth frequency component-enhanced images. For example, in the second and third frequency component-enhanced images in which a lot of the deep blood vessel and the BA are included, since the deep blood vessel and the BA are a down edge where the value of the image falls below "0", it is preferable that Gain2(RGB) and Gain3(RGB) are set to negative values.

For the pixels where the B/G ratio and the G/R ratio are included in the second range, the composition ratio setting unit 75*b* sets the composition ratio g1 (the B/G ratio and the G/R ratio) to "100%" and sets the composition ratios g2, g3, and g4 (the B/G ratio and the G/R ratio) to "0%"; thus, for the pixels in the color difference-enhanced image where the B/G ratio and the G/R ratio are within the second range, a first frequency-enhanced component is added. Since a lot of the B/G ratio and the G/R ratio of the atrophic mucosa area are included in the second range, it is possible to enhance the structure of the atrophic mucosa with the addition of the first frequency-enhanced component.

For the pixels where the B/G ratio and the G/R ratio are included in the third range, the composition ratio setting unit 75*b* sets the composition ratio g2 (the B/G ratio and the G/R ratio) to "100%", and sets the composition ratios g1, g3, and g4 (the B/G ratio and the G/R ratio) to "0%"; thus, for the pixels in the color difference-enhanced image where the B/G ratio and the G/R ratio are within the third range, a second frequency-enhanced component is added. Since a lot of the B/G ratio and the G/R ratio of the deep blood vessel area are included in the third range, it is possible to enhance the structure of the deep blood vessel area with the addition of the second frequency-enhanced component.

For the pixels where the B/G ratio and the G/R ratio are included in the fourth range, the composition ratio setting unit 75*b* sets the composition ratio g3 (the B/G ratio and the G/R ratio) to "100%", and sets the composition ratios g1, g2, and g4 (the B/G ratio and the G/R ratio) to "0%"; thus, for the pixels in the color difference-enhanced image where the B/G ratio and the G/R ratio are within the fourth range, a third frequency-enhanced component is added. Since a lot of the B/G ratio and the G/R ratio of the BA are included in the fourth range, it is possible to enhance the structure of the BA with the addition of the third frequency-enhanced component.

For the pixels where the B/G ratio and the G/R ratio are included in the fifth range, the composition ratio setting unit 75b sets the composition ratio g4 (the B/G ratio and the G/R ratio) to "100%", and sets the composition ratios g1, g2, and g3 (the B/G ratio and the G/R ratio) to "0%"; thus, for the pixels in the color difference-enhanced image where the B/G ratio and the G/R ratio are within the fifth range, a fourth frequency-enhanced component is added. Since a lot of the B/G ratio and the G/R ratio of the reddened area are included in the fourth range, it is possible to enhance the structure of the reddened area with the addition of the fourth frequency-enhanced component.

As described above, the composition ratios are set for the respective pixels based on the B/G ratio and the G/R ratio, and the frequency component-enhanced images are composed with the color difference-enhanced image at the composition ratios set for the respective pixels, whereby it is possible to selectively enhance the atrophic mucosa area, the deep blood vessel area, the BA, or reddened area. For example, in a case where the first or third frequency component-enhanced image is added to all pixels of the color difference-enhanced image regardless of the B/G ratio and the G/R ratio, since the first or third frequency component image is an image in which a low frequency component is enhanced, both of the atrophic mucosa and the BA are enhanced. Accordingly, as in the invention, the first frequency component-enhanced image is added only to the pixels in the color difference-enhanced image where the B/G ratio and the G/R ratio are within the second range, whereby it is possible to enhance only the atrophic mucosa without enhancing the BA. In contrast, the third frequency component-enhanced image is added only to the pixels in the color difference-enhanced image where the B/G ratio and the G/R ratio are within the fourth range, whereby it is possible to enhance only the atrophic mucosa without enhancing the BA.

The inverse Log conversion unit 76 subjects the RGB image signals of the color difference and structure-enhanced image to inverse Log conversion. With this, the RGB image signals of the color difference and structure-enhanced image having an antilogarithmic pixel value are obtained. The gamma conversion unit 77 subjects the RGB image signals of the color difference and structure-enhanced image having an antilogarithmic pixel value to gamma conversion. With this, the RGB image signals of the color difference and structure-enhanced image having gradation suitable for an output device, such as the monitor 18, are obtained. The color difference and structure-enhanced image is transmitted to the video signal generation unit 66 as a special image.

Figure 13:
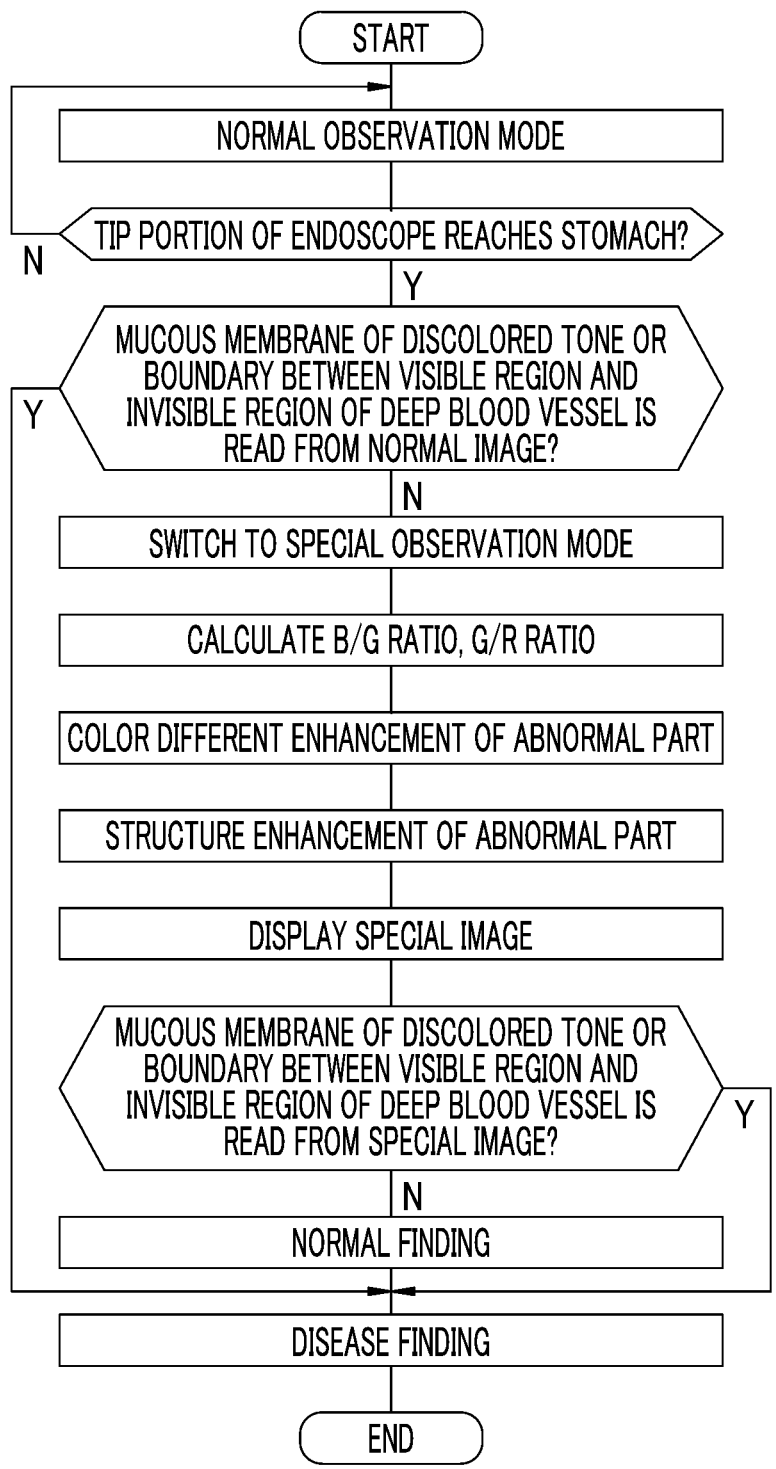
FIG. 13 is a flowchart showing a series of flow in diagnosis of atrophic gastritis.

Next, a series of flow in this embodiment will be described along the flowchart of FIG. 13. First, the normal observation mode is set, and the insertion portion 21 of the endoscope 12 is inserted into the specimen. After the tip portion 24 of the insertion portion 21 reaches the stomach, diagnosis is performed regarding whether or not atrophic gastritis occurs. In a case where the boundary (also referred to as an endoscopic boundary) between a part where a mucosa is faded or a dendritic deep blood vessel becomes see-through and a part where a dendritic deep blood vessel does not become see-through can be read from the normal image, the doctor determines a disease fining that a lesion, such as a gastric cancer, is caused by atrophic gastritis (a determination method according to Kimura-Takemoto classification). It is understood that the gastric cancer is caused by atrophy of a gastric mucosa due to infection with *pylori*.

In a case where the presence of the faded mucosa or the endoscopic boundary cannot be read from the normal image, in order to more reliably perform diagnosis, the mode selection SW 22b is operated to switch the observation mode to the special observation mode. With the switching to the special observation mode, special light including both of the blue laser beam and the violaceous laser beam is emitted. The B/G ratio and the G/R ratio are calculated from the RGB image signals obtained at the time of emission of special light.

Next, the color difference enhancement amounts corresponding to the calculated B/G ratio and G/R ratio are determined with reference to the two-dimensional LUT 73a. The enhancement coefficient f(R) is determined from the R image signal. The color difference enhancement amounts multiplied by the enhancement coefficient f(R) are added to the B/G ratio and the G/R ratio to obtain the B/G ratio and the G/R ratio subjected to color difference enhancement.

Next, the B/G ratio and the G/R ratio subjected to color difference enhancement are converted to the RGB image signals. The RGB image signals are subjected to a plurality of kinds of frequency filtering to obtain the first to fourth frequency component-enhanced images. The composition ratios g1 to g4 (the B/G ratio and the G/R ratio) are determined from the B/G ratio and the G/R ratio for the respective pixels. The first to fourth frequency component-enhanced images multiplied by Gain1 (RGB) to Gain4 (RGB) and the composition ratios g1 to g4 (the B/G ratio and the G/R ratio) are added to the RGB image signals subjected to color difference enhancement to obtain the RGB image signals subjected to color different and structure enhancement. A special image is displayed on the monitor 18 based on the RGB image signals subjected to color difference and structure enhancement.

In a case where there is no atrophy of the stomach, a mucosa is displayed in a color as normal on the special image. In this case, the doctor determines a normality finding that there is no occurrence of a lesion part, such as a gastric cancer due to atrophic gastritis. In contrast, even in a case where atrophy of the stomach is progressing slightly, the color of an atrophic mucosa is displayed faded, a deep blood vessel is displayed see-through, and the structure of the atrophic mucosa or the deep blood vessel is enhanced. With this, it is possible to clearly display the endoscopic boundary. Accordingly, the color of the atrophic mucosa is not particularly displayed faded in the actual stomach, and even in a case where the deep blood vessel does not become so see-through, the doctor can determine a disease finding that a lesion, such as a gastric cancer, occurs due to atrophic gastritis.

Figure 14:
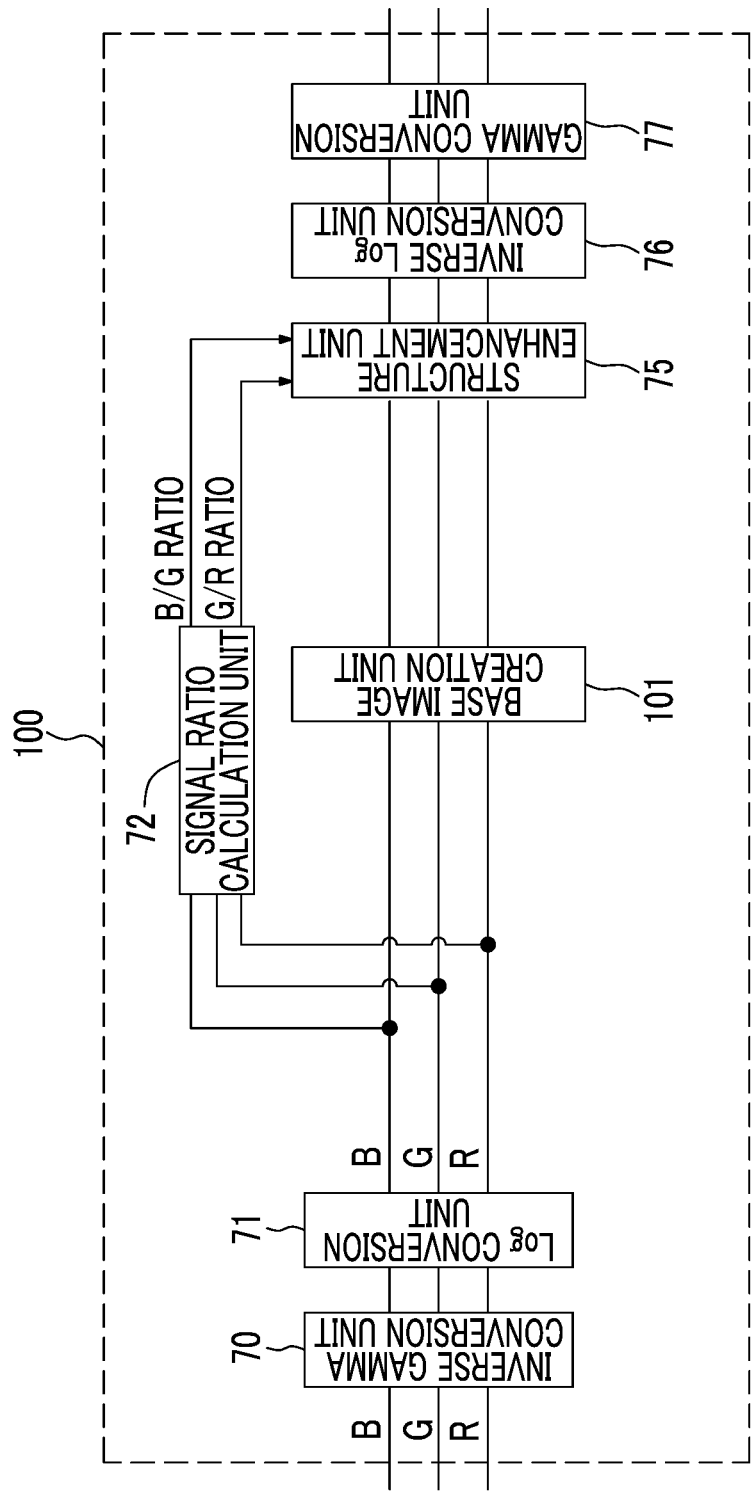
FIG. 14 is a block diagram showing the functions of a special image processing unit different from FIG. 4.

In the foregoing embodiment, although the structure enhancement processing is performed on the color difference-enhanced image in which the color difference between the normal part and the abnormal part is enhanced to generate the color difference and structure-enhanced image, the invention is not limited thereto, the structure enhancement processing may be performed directly to generate a structure-enhanced image without performing color difference enhancement. In this case, a special image processing unit 100 shown in FIG. 14 is used, instead of the special image processing unit 64 of the FIG. 2. The special image processing unit 100 is not provided with the color difference enhancement unit 73 and the RGB conversion unit 74, unlike the special image processing unit 64. The special image processing unit 100 is provided with a base image creation unit 101 between the Log conversion unit 71 and the structure enhancement unit 75.

In the special image processing unit 100, the base image creation unit 101 creates a base image based on the RGB image signals subjected to Log conversion in the Log conversion unit 71. The base image is transmitted to the structure enhancement unit 75. The RGB image signals subjected to Log conversion are transmitted to the signal ratio calculation unit 72. The signal ratio calculation unit 72 calculates the B/G ratio and the G/R ratio based on the RGB image signals and transmits the calculated B/G ratio and G/R ratio to the structure enhancement unit 75. The structure enhancement unit 75 generates a structure-enhanced image, in which the structure of an atrophic mucosa, a deep blood vessel, or a BA is selectively enhanced, based on the RGB image signals of the base image and the B/G ratio and the G/R ratio.

In the above-described embodiment, although the B/G ratio and the G/R ratio are subjected to polar coordinate conversion, and the radius vector difference or the deflection angle difference between the first range average value subjected to the polar coordinate conversion and the signal values in the second to fifth ranges is expanded to enhance the difference in color between the normal part and the abnormal part, the invention is not limited thereto, and the difference in color between the normal part and the abnormal part may be enhanced using other coordinate conversion methods and color difference enhancement methods. As in the foregoing embodiment, in the color difference-enhanced image obtained using the color difference enhancement method which expands the radius vector difference or the deflection angle difference on the polar coordinates, since only the color of the abnormal part can be changed without changing the color of the normal part so much, a sense of discomfort is not caused. Since the color of the atrophic mucosa area or the deep blood vessel area on the color difference-enhanced image is the same as a color of a mucosa when atrophic gastritis occurs or a color when the blood vessel becomes see-through, it is possible to perform diagnosis by the same method as atrophic gastritis diagnosis (for example, ABC examination).

In the above-described embodiment, although the first range average value is used for color difference enhancement of the normal part and the abnormal part, alternatively, the average value of the pixel values of the entire image signal may be used. In this case, while there is a concern that the color of the atrophic mucosa or the deep blood vessel fluctuates for the respective pixels, there is an advantage capable of expanding the slight difference in color between the normal part and the abnormal part according to the distribution of each area on the image.

In the first embodiment described above, although the phosphor 44 is provided in the tip portion 24 of the endoscope 12, alternatively, the phosphor 44 may be provided in the light source device 14. In this case, it is preferable that the phosphor 44 is provided between the light guide 41 and the blue laser source 34.

Second Embodiment

Figure 15:
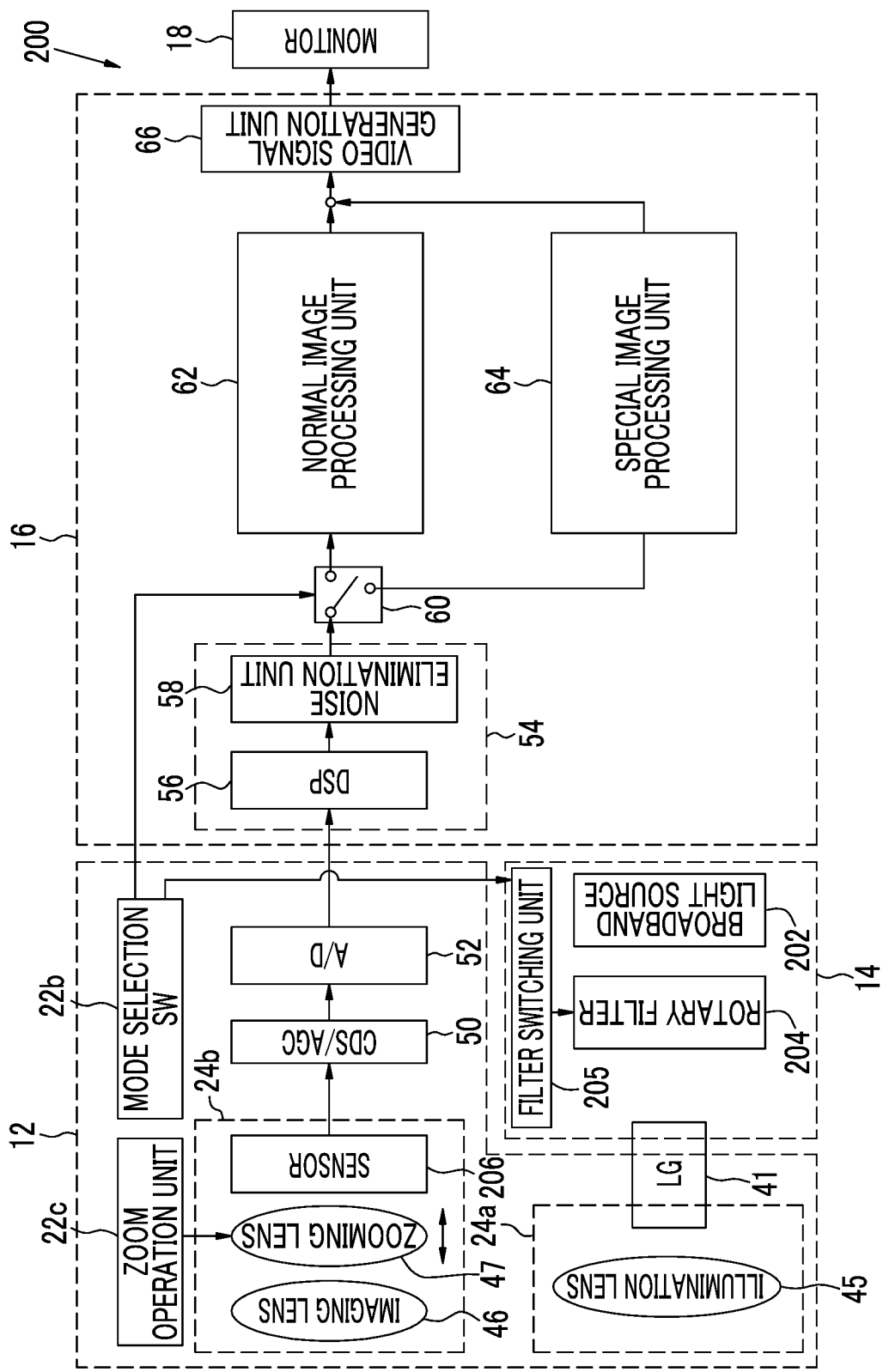
FIG. 15 is a block diagram showing the internal configuration of an endoscope system of a second embodiment.

In the first embodiment described above, although the RGB image signals are acquired simultaneously with the color sensor, in a second embodiment, the RGB image signals are acquired sequentially with a monochrome sensor. As shown in FIG. 15, a light source device 14 of an endoscope system 200 of the second embodiment is provided with a broadband light source 202, a rotary filter 204, and a filter switching unit 205, instead of the blue laser source 34, the violaceous laser source 36, and the light source control unit 40. The phosphor 44 is not provided in the illumination optical system 24a of the endoscope 12. The imaging optical system 24b is provided with a monochrome sensor 206 with no color filters, instead of the color sensor 48. Other parts are the same as those in the endoscope system 10 of the first embodiment.

The broadband light source 202 is a Xenon lamp, a white LED, or the like, and emits white light having a wavelength band from blue to red. The rotary filter 204 comprises an internal filter 208 for a normal observation mode and an external filter 209 for a special observation mode (see FIG. 16). The filter switching unit 205 moves the rotary filter 204 in a radius direction, inserts the filter 208 for a normal observation mode of the rotary filter 204 into the optical path of white light when the normal observation mode is set by the mode selection SW 22b, and inserts the filter 209 for a special observation mode of the rotary filter 204 into the optical path of white light when the special observation mode is set.

Figure 16:
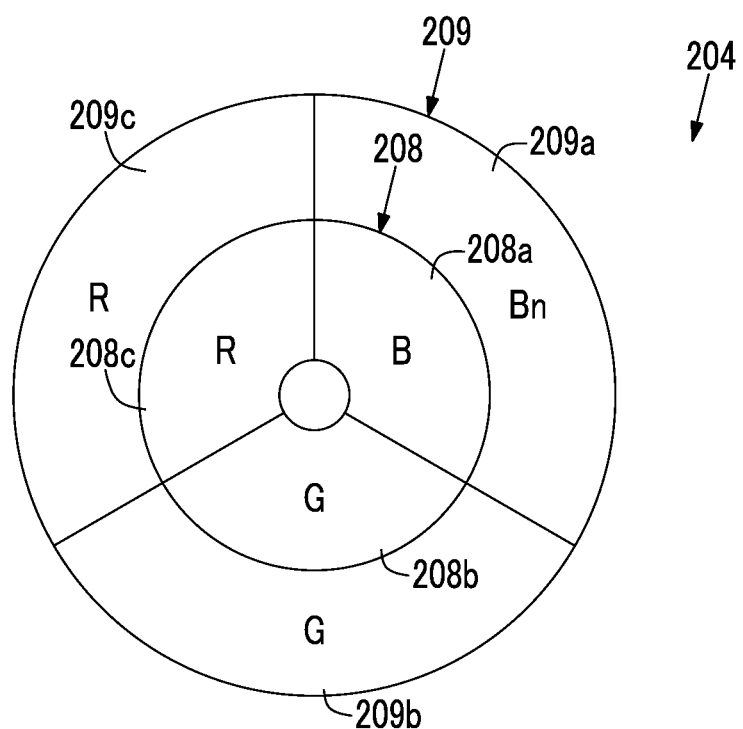
FIG. 16 is a plan view of a rotary filter.

As shown in FIG. 16, the filter 208 for a normal observation mode is provided with, in a circumferential direction, a B filter 208a which transmits blue light from white light, a G filter 208b which transmits green light from white light, and an R filter 208c which transmits red light from white light. Accordingly, in the normal observation mode, the rotary filter 204 rotates, whereby the inside of the specimen is alternately irradiated with blue light, green light, and red light.

The filter 209 for a special observation mode is provided with, in a circumferential direction, a Bn filter 209a which transmits blue narrowband light having a center wavelength of 415 nm from white light, a G filter 209b which transmits green light from white light, and an R filter 209c which transmits red light from white light. Accordingly, in the special observation mode, the rotary filter 204 rotates, whereby the inside of the specimen is alternately irradiated with blue narrowband light, green light, and red light.

In the endoscope system 200, in the normal observation mode, the inside of the specimen is imaged by the monochrome sensor 206 each time the inside of the specimen is irradiated with blue light, green light, and red light. With this, image signals of three colors of RGB are obtained. A normal image is generated based on the image signals of RGB by the same method as in the foregoing first embodiment.

In the special observation mode, the inside of the specimen is imaged by the monochrome sensor 206 each time the inside of the specimen is irradiated with blue narrowband light, green light, and red light. With this, a Bn image signal, a G image signal, and an R image signal are obtained. A special image is generated based on the Bn image signal, the G image signal, and the R image signal. In generating the special image, the Bn image signal is used, instead of the B image signal. Except for this, the generation of the special image is performed by the same method as in the first embodiment.

Third Embodiment

In the endoscope system 10 of the first embodiment, the B image signal which is a narrowband signal including narrowband wavelength information of the blue laser beam and the violaceous laser beam is used to create the special image, and in the endoscope system 200 of the second embodiment, the Bn image signal which is a narrowband signal including narrowband wavelength information of blue narrowband light is used to create the special image; however, in a third embodiment, a blue narrowband image signal is generated by spectral calculation based on a broadband image, such as a white image, and a special image is generated using the blue narrowband image signal.

Figure 17:
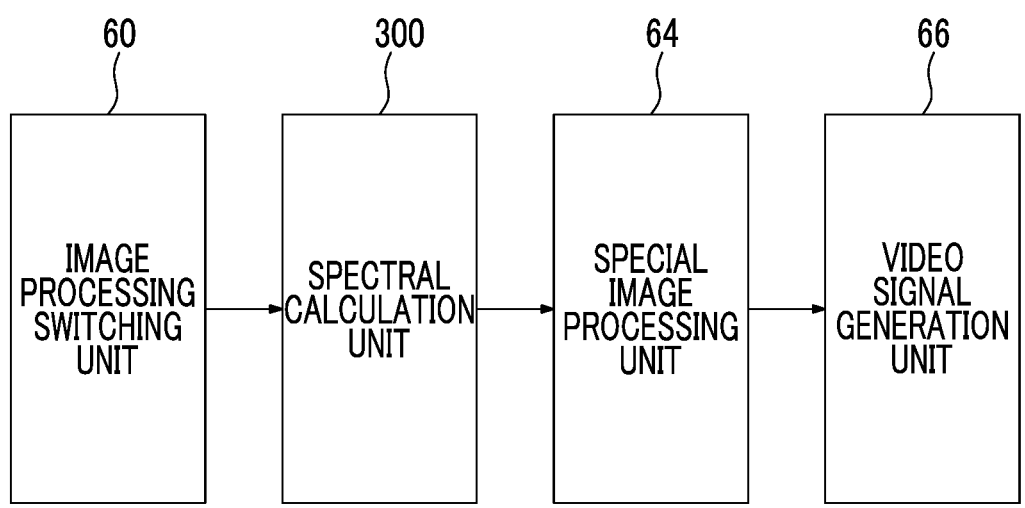
FIG. 17 is a block diagram showing a part of functions in a processor device in a third embodiment.
Figure 18A:
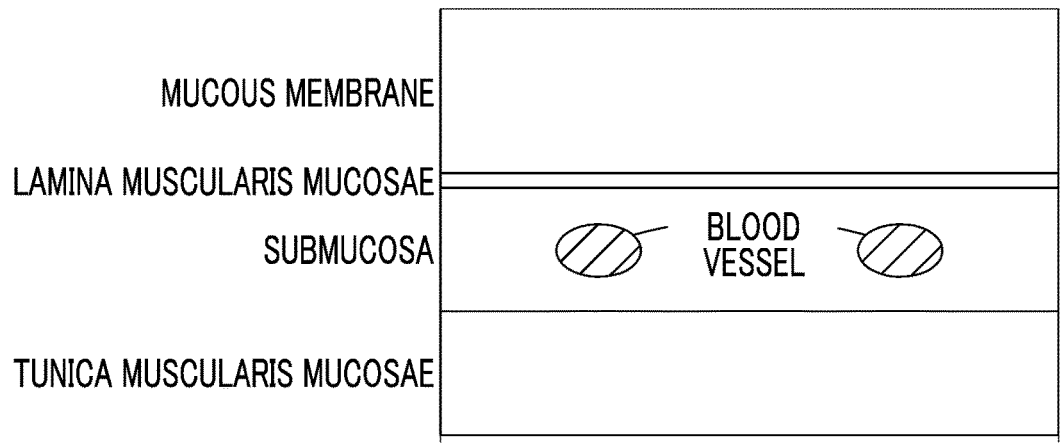
FIG. 18A is a sectional view of a mucosal structure in a normal mucosa.
Figure 18B:
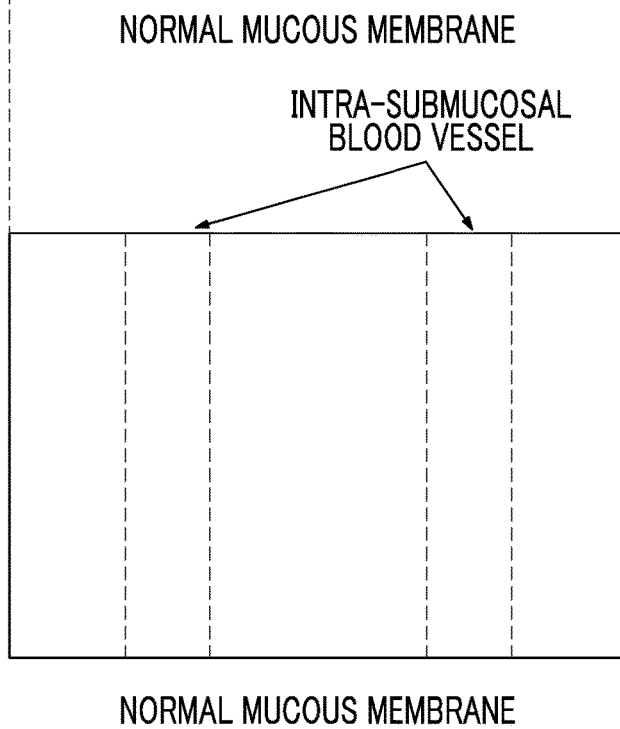
FIG. 18B is a plan view when a normal mucosa is viewed from a surface layer side.
Figure 19A:
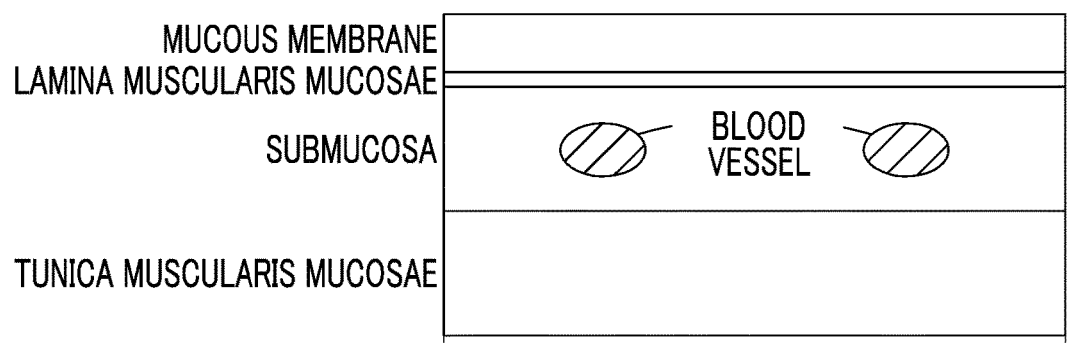
FIG. 19A is a sectional view of a mucosal structure (a gastric mucosal layer is thinned due to a decrease in the number of gastric gland cells or substitution of gastric tissue and intestine or fiber structure) at the time of atrophic gastritis.
Figure 19B:
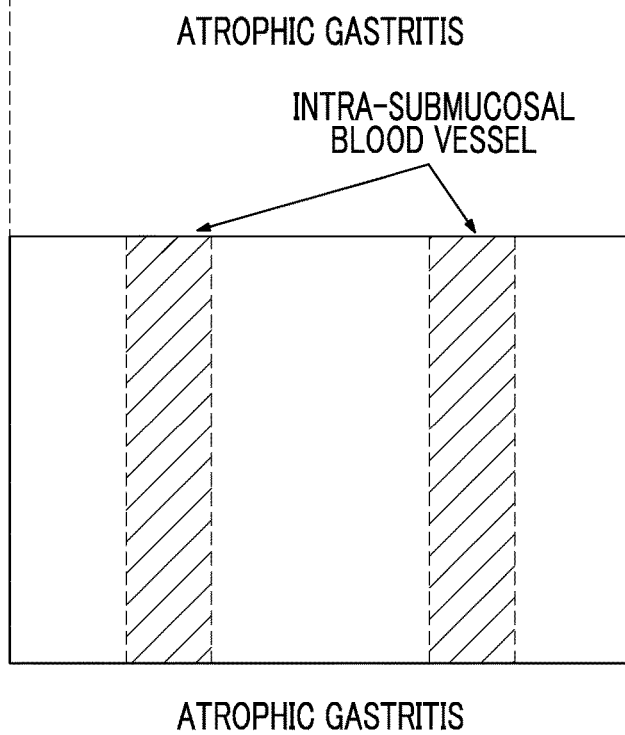
FIG. 19B is a plan view when a mucosa at the time of atrophic gastritis is viewed from a surface layer side.

In the third embodiment, white light which is broadband light is illuminated instead of special light in the special observation mode of the simultaneous endoscope system 10. As shown in FIG. 17, in a spectral calculation unit 300 provided between the image processing switching unit 60 and the special image processing unit 64, spectral calculation processing based on RGB image signals obtained through white light emission and imaging is performed. With this, a blue narrowband image signal which is a spectral image having a wavelength band of 400 to 420 nm is generated. As a method of spectral calculation, a method described in JP2003-093336A is used. A special image is generated based on the blue narrowband image signal generated by the spectral calculation unit 300, the G image signal, and the R image signal by the same procedure as in the foregoing first embodiment. As white light, in addition to white light obtained by the phosphor 44, broadband light emitted from a broadband light source, such as a Xenon lamp, may be used.

In the foregoing embodiments, although an example where a mucosa is faded due to atrophic gastritis and an example where a deep blood vessel under an atrophic mucosa becomes see-through have been described, there is a case where a mucosa is faded due to a lesion of a different region (for example, a lesion of esophagus, a lesion of large intestine, or the like). According to the invention, in regard to a faded mucosa other than an atrophic mucosa, it is possible to enhance the color difference from a normal part. Furthermore, according to the invention, it is possible to enhance and display seeing-through of a deep blood vessel under a faded mucosa other than an atrophic mucosa.

In the foregoing embodiments, although the B/G ratio and the G/R ratio are used as a plurality of kinds of color information, alternatively, a color difference signal Cr and a color difference signal Cb may be used. In this case, color difference enhancement of a normal part and an abnormal part or structure enhancement of an abnormal part is performed using a CrCb space which is a feature space formed from the color difference signals Cr and Cb. Hue H and saturation S may be used as a plurality of kinds of color information. In this case, color difference enhancement of a normal part and an abnormal part or structure enhancement of an abnormal part is performed using an HS space which is a feature space formed from hue H and saturation S. The elements a* and b* of tint of a CIE Lab space may be used as a plurality of kinds of color information. In this case, color difference enhancement of a normal part and an abnormal part or structure enhancement of an abnormal part is performed using an ab space which is a feature space formed from the elements a* and b*.

In the foregoing embodiments, although the invention has been carried out during endoscopic diagnosis, the invention is not limited thereto, and the invention may be carried out based on an endoscopic image recorded in a recording unit of an endoscope system after endoscopic diagnosis, or the invention may be carried out based on a capsule endoscopic image acquired by a capsule endoscope.

Although the present invention has been fully described by the way of the preferred embodiment thereof with reference to the accompanying drawings, various changes and modifications will be apparent to those having skill in this field. Therefore, unless otherwise these changes and modifications depart from the scope of the present invention, they should be construed as included therein.

What is claimed is:

1. An image processing device comprising:
an image signal input unit which inputs image signals of three colors;
a base image creation unit which creates a base image based on the image signals of three colors;
a signal ratio calculation unit which calculates a first signal ratio between the image signals of two colors among the image signals of the three colors and a second signal ratio between the image signals of two colors different from the colors for the first signal ratio;
a frequency enhancement unit which generates a frequency component-enhanced image, in which a frequency component corresponding to an abnormal part different from a normal part is enhanced, based on the base image;
a composition ratio setting unit which sets a composition ratio indicating the ratio for composing the frequency component-enhanced image with the base image based on the first signal ratio and the second signal ratio; and
a composition unit which composes the frequency component-enhanced image with the base image at the composition ratio set by the composition ratio setting unit to generate a structure-enhanced image, in which the structure of the abnormal part is enhanced.

2. The image processing device according to claim 1, wherein the composition ratio setting unit sets the composition ratio to 0% for pixels where the first and second signal ratios calculated by the signal ratio calculation unit are included in a first range having the first and second signal ratios of the normal part, and sets the composition ratio to 100% for pixels where the first and second signal ratios calculated by the signal ratio calculation unit are included in a specific range having the first and second signal ratios of the abnormal part.

3. The image processing device according to claim 2, wherein the abnormal part is a faded mucosa,
the specific range is a second range which includes the first and second signal ratios of the faded mucosa, and
the first range and the second range have the same hue, and the second range has saturation lower than that in the first range.

4. The image processing device according to claim 2, wherein the abnormal part is a blood vessel area which has a blood vessel, which becomes see-through with the progress of a lesion under a faded mucosa,
the specific range is a third range which includes the first and second signal ratios of the blood vessel area, and
the first range and the third range have the same saturation and have different hues.

5. The image processing device according to claim 2, wherein the abnormal part is a brownish area, and
the specific range is a fourth range which includes the first and second signal ratios of the brownish area.

6. The image processing device according to claim 2, wherein the abnormal part is reddened area, and
the specific range is a fifth range which includes the first and second signal ratios of the reddened area.

7. The image processing device according to claim 1, wherein the image signals of the three colors are RGB image signals, and
the first signal ratio is a B/G ratio between the B image signal and the G image signal, and the second signal ratio is a G/R ratio between the G image signal and the R image signal.

8. An image processing device comprising:
an image signal input unit which inputs a color image signal;
a color information acquisition unit which acquires a plurality of kinds of color information from the color image signal;
a color difference enhancement unit which performs expansion processing for expanding the difference between a first range and a specific range different from the first range in a feature space formed by the plurality of kinds of color information to generate a color difference-enhanced image, in which the color difference between a normal part and an abnormal part is enhanced;
a frequency enhancement unit which generates a frequency component-enhanced image, in which a frequency component corresponding to the abnormal part is enhanced, based on the color difference-enhanced image;
a composition ratio setting unit which sets a composition ratio indicating the ratio for composing the frequency component-enhanced image with the color difference-enhanced image based on the plurality of kinds of color information; and
a composition unit which composes the frequency component-enhanced image with the color difference-enhanced image at the composition ratio set by the composition ratio setting unit to generate a color difference and structure-enhanced image, in which the color difference is enhanced and the structure of the abnormal part is enhanced.

9. The image processing device according to claim 8, wherein the color image signal is image signals of three colors, and the color information acquisition unit is a signal ratio calculation unit which calculates, as the plurality of kinds of color information, a first signal ratio between the image signals of two colors among the image signals of the three colors and a second signal ratio between the image signals of two colors different from the colors for the first signal ratio.

10. The image processing device according to claim 9, wherein the composition ratio setting unit sets the composition ratio to 0% for pixels where the first and second signal ratios calculated by the signal ratio calculation unit are included in the first range, and sets the composition ratio to 100% for pixels where the first and second signal ratios calculated by the signal ratio calculation unit are included in the specific range.

11. The image processing device according to claim 10, wherein the abnormal part is a faded mucosa,
the specific range is a second range which includes the first and second signal ratios of the faded mucosa, and
the first range and the second range have the same hue, and the second range has saturation lower than that in the first range.

12. The image processing device according to claim 10, wherein the abnormal part is a blood vessel area which has a blood vessel, which becomes see-through with the progress of a lesion under a faded mucosa,
the specific range is a third range which includes the first and second signal ratios of the blood vessel area, and
the first range and the third range have the same saturation and have different hues.

13. The image processing device according to claim 10, wherein the abnormal part is a brownish area, and
the specific range is a fourth range which includes the first and second signal ratios of the brownish area.

14. The image processing device according to claim 10, wherein the abnormal part is reddened area, and
the specific range is a fifth range which includes the first and second signal ratios of the reddened area.

15. The image processing device according to claim 9, wherein the image signals of the three colors are RGB image signals, and
the first signal ratio is a B/G ratio between the B image signal and the G image signal, and the second signal ratio is a G/R ratio between the G image signal and the R image signal.

16. An operation method for an image processing device comprising:
a step in which an image signal input unit inputs image signals of three colors;
a step in which a base image creation unit creates a base image based on the image signals of three colors;
a step in which a signal ratio calculation unit which calculates a first signal ratio between the image signals of two colors among the image signals of the three colors and a second signal ratio between the image signals of two colors different from the colors for the first signal ratio;
a step in which a frequency enhancement unit generates a frequency component-enhanced image, in which a frequency component corresponding to an abnormal part different from a normal part is enhanced, based on the base image;
a step in which a composition ratio setting unit sets a composition ratio indicating the ratio for composing the frequency component-enhanced image with the base image based on the first signal ratio and the second signal ratio; and
a step in which a composition unit composes the frequency component-enhanced image with the base image at the composition ratio set by the composition ratio setting unit to generate a structure-enhanced image, in which the structure of the abnormal part is enhanced.

17. An operation method for an image processing device comprising:
a step in which an image signal input unit inputs a color image signal;
a step in which a color information acquisition unit acquires a plurality of kinds of color information from the color image signal;
a step in which a color difference enhancement unit performs expansion processing for expanding the difference between a first range and a specific range different from the first range in a feature space formed by the plurality of kinds of color information to generate a color difference-enhanced image, in which the color difference between a normal part and an abnormal part is enhanced;
a step in which a frequency enhancement unit generates a frequency component-enhanced image, in which a frequency component corresponding to the abnormal part is enhanced, based on the color difference-enhanced image;
a step in which a composition ratio setting unit sets a composition ratio indicating the ratio for composing the frequency component-enhanced image with the color difference-enhanced image based on the plurality of kinds of color information; and
a step in which a composition unit composes the frequency component-enhanced image with the color difference-enhanced image at the composition ratio set by the composition ratio setting unit to generate a color difference and structure-enhanced image, in which the color difference is enhanced and the structure of the abnormal part is enhanced.

* * * * *